United States Patent
Morris et al.

(10) Patent No.: US 6,927,220 B2
(45) Date of Patent: Aug. 9, 2005

(54) BICYCLIC-SUBSTITUTED 4-AMINO-PYRIDOPYRIMIDINE DERIVATIVES

(75) Inventors: Joel Morris, East Lyme, CT (US); Samit K. Bhattacharya, Groton, CT (US); John C. Kath, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/121,831

(22) Filed: Apr. 12, 2002

(65) Prior Publication Data

US 2003/0045535 A1 Mar. 6, 2003

Related U.S. Application Data

(60) Provisional application No. 60/283,910, filed on Apr. 13, 2001.

(51) Int. Cl.[7] .................. C07D 471/04; A61K 31/519; A61P 35/00
(52) U.S. Cl. ................................. 514/264.11; 544/279
(58) Field of Search ...................... 544/279; 514/264.11

(56) References Cited

U.S. PATENT DOCUMENTS

| | | | |
|---|---|---|---|
| 6,123,939 A | | 9/2000 | Shawver |
| 6,297,238 B1 | * | 10/2001 | Doyle et al. ............. 514/232.8 |
| 6,492,383 B1 | * | 12/2002 | Munchhof et al. .......... 514/301 |
| 2005/0038047 A1 | * | 2/2005 | Edwards et al. ....... 514/264.11 |

FOREIGN PATENT DOCUMENTS

| | | |
|---|---|---|
| GB | 2345486 | 7/1999 |
| WO | WO 9640142 | 12/1993 |
| WO | WO 9519774 | 7/1995 |
| WO | WO9521613 * | 8/1995 |
| WO | WO 9713771 | 4/1997 |
| WO | WO 9738983 | 10/1997 |
| WO | WO 9802437 | 1/1998 |
| WO | WO 9802438 | 1/1998 |
| WO | WO 9935132 | 7/1999 |
| WO | WO 9935146 | 7/1999 |
| WO | WO 0104111 | 1/2001 |

OTHER PUBLICATIONS

Receptor Tyrosine Kinases (RTKs) chart from http://www.kinase.com/mammalian/rtks.pdf downloaded from the Internet Feb. 26, 2004.*
Abstract of Kelloff, Cancer Epidemiol Biomarkers Prevention, vol. 5, (8) pp. 657–666, 1966.*
Abstract of Lemoine et al, J.Patho1, Jan. 1992, 166(1) 7–12.*
Abstract of Stephan et al., Puerto Rico Health Sciences Journal, vol. 15( 3) pp. 169–178, 1996.*
Sariola Nature Medicine, vol. 5, No. 1, Jan. 1999.*
Holt, http://www.biopathics.com/neutriceuticals2[1].htm.*
Angiogenesis by Kate L Pugh www.earth.li/~kake/maths/mathbiol/angiogenesis.html.*
Jiang, Journal of Biological Chemistry, vol. 278, No. 34, pp. 31964–31971, 2003.*
Abstract of Chou et al Circulation. 105 (3): 373, 2002.*
R. Roskoski, *BBRC*,vol. 319 (2004): 1–11 "The ErbB/HER receptor protein–tyrosine kinases and cancer."
European Search Report for European Patent Application No. EP 02 25 2428; 2 pages.

* cited by examiner

*Primary Examiner*—Mark L. Berch
(74) *Attorney, Agent, or Firm*—Peter C. Richardson; Garth Butterfield; Christian M. Smolizza

(57) ABSTRACT

The invention relates to 6- or 7-bicyclic-substituted 4-amino-subsituted pyridopyrimidines and to pharmaceutically acceptable salts, prodrugs and hydrates thereof. The invention also relates to pharmaceutical compositions containing the compounds and to methods of treating hyperproliferative disorders abnormal cell growth in a mammal by administering the compounds.

29 Claims, No Drawings

BICYCLIC-SUBSTITUTED 4-AMINO-PYRIDOPYRIMIDINE DERIVATIVES

This application claims the benefit of U.S. Provisional Application No. 60/283,910, filed Apr. 13, 2001.

BACKGROUND OF THE INVENTION

This invention relates to novel bicyclic-substituted pyridopyrimidine derivatives. These derivatives are useful in the treatment of abnormal cell growth, such as cancers, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. The erbB-2 protein, e.g. c-erbB-2, is a receptor tyrosine kinase which is homologous to the epidermal growth factor (EGF) receptor. Other receptor tyrosine kinases include c-met, tie-2, PDGFr, FGFr, and VEGFR. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or over-expressed in many human cancers such as brain, lung, squamous cell, bladder, gastric, breast, head and neck, oesophageal, gynecological and thyroid tumors. In particular, clinical and experimental evidence suggests a role for overexpression of the erbB-2 protein in the progression of human breast, ovarian and non-small lung carcinomas. For example, amplification and/or overexpression of the erbB-2 gene have been shown in adenocarcinomas of the breast, ovary, lung and stomach. In breast carcinoma, a correlation has been observed between gene amplification and overexpression of erbB-2 protein and the aggressiveness of the malignancy (Slamon et al, Science, (1987), 237, 177–182; Slamon et al, Science, (1989), 244, 707–712). The overexpression of erbB-2 has also been directly linked to the malignant conversion of cancer cells. Inhibition of the erbB2 receptor by monoclonal antibodies have been found to inhibit the proliferation of a human breast carcinoma cell line in human tissue culture (Hudziak et al, Mol. Cell. Biol., (1989), 9, 1165–1172), and an antibody directed to the rat erbB-2 protein, has been reported to inhibit the tumorigenicity of fibroblasts transformed by the mutant rat erbB-2 oncogene (Drebin et al, Proc. Nat'l. Acad. Sci., (1986), 83, 9126–9133; Drebin etal, Oncogene, (1988), 2, 387–399).

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma which expresses epidermal growth factor receptor tyrosine kinase (EGFR) but is without effect on the growth of another carcinoma which does not express the EGF receptor. Thus, the compounds of the present invention, which are selective inhibitors of erbB-2 receptor tyrosine kinases, are useful in the treatment of abnormal cell growth, in particular cancer, in mammals.

Compounds which are ErbB2 receptor inhibitors include GW-282974 (Glaxo Wellcome plc), and the monoclonal antibodies AR-209 (Aronex Pharmaceuticals Inc. of The Woodlands, Tex. USA) and 2B-1 (Chiron), for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. application Ser. No. 09/488,350 (filed Jan. 20, 2000), and in U.S. application Ser. No. 09/488,378 (filed Jan. 20, 2000), both of which are incorporated in their entireties herein by reference.

Other compounds that are useful in the treatment of hyperproliferative diseases are also disclosed in the following co-pending patent applications: PCT international patent application WO 97/49688 (published Dec. 31, 1997), U.S. patent application Ser. No. 09/308,602 (filed Nov. 5, 1997), U.S. patent application Ser. No. 08/953,078 (filed Oct. 17, 1997), U.S. patent application Ser. No. 08/653,786 (filed May 28, 1996), PCT international patent application publication number WO 96/40142 (published Dec. 19, 1996), PCT international patent application publication number WO 97/13771 (published Apr. 17, 1997), and PCT international patent application publication number WO 95/23141 (published Aug. 31, 1995). Each of the foregoing United States and PCT international patent applications is incorporated herein by reference in its entirety.

SUMMARY OF THE INVENTION

The present invention relates to compounds of the formula 1

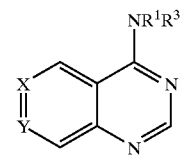

and to pharmaceutically acceptable salts, prodrugs and hydrates thereof, wherein:

each $R^1$ and $R^2$ is independently H or $(C_1-C_6)$alkyl;

$R^3$ is $—(CR^1R^2)_m—R^4$, wherein m is an integer from 0 to 6; or $—NR^1R^3$ taken together form a group having the formula

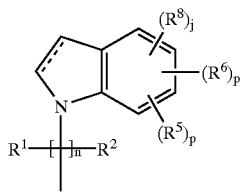

each n is independently an integer from 0 to 4; each p is independently 0 or 1; each j is independently an integer from 0 to 2; and the dotted line represents an optional carbon-carbon bond;

either X is N and Y is $CR^9$, or X is $CR^9$ and Y is N (i.e., the two adjoining atoms —X=Y— are either —N=$CR^9$— or —$CR^9$=N—);

$R^4$ is aryl or heteroaryl, wherein the aryl or heteroaryl is optionally substituted on one carbon atom with $R^5$, -$Z^1R^5$, -$Z^1(CR^1R^2)_rR^5$ or —$(CR^1R^2)_rR^5$, optionally substituted on another carbon atom with $R^6$ and optionally substituted on any remaining carbon atoms independently with $R^8$;

$Z^1$ is $S(O)_j$, O, or $NR^1$, provided that when -$Z^1R^5$ is —$NR^1R^5$, $R^5$ is linked to N by a carbon atom; each j is independently an integer from 0 to 2; each r is independently an integer from 1 to 4;

$R^5$ is aryl, heteroaryl or heterocyclyl, wherein the aryl, heteroaryl or heterocyclyl is optionally substituted on one carbon atom with $R^6$ and optionally substituted on up to three other carbon atoms independently with $R^8$, and wherein when $R^5$ is heterocyclyl, the heterocyclyl is optionally substituted on up to two nitrogen atoms independently with $R^7$;

each $R^6$ is independently $(C_1-C_6)$alkyl, $(C_2-C_6)$alkenyl, $(C_2-C_6)$alkynyl, $(C_3-C_8)$cycloalkyl, $(C_1-C_6)$alkoxy, $(C_1-C_6)$alkylthio, hydroxy$(C_1-C_6)$alkyl, trifluoromethyl, trifluoromethyl$(C_2-C_6)$alkyl, trifluoromethoxy, trifluoro$(C_2-C_6)$alkoxy, —$(CR^1R^2)_nO(C_1-C_6$ alkyl), —$(CR^1R^2)_nS(O)_j(C_1-C_6$ alkyl), halo, hydroxy, cyano, nitro, azido, amino, —$(CR^1R^2)_nNR^1R^7$, —$C(O)NR^1R^7$, —$NR^7C(O)R^{11}$, —$NR^7OR^{14}$, —$NR^7C(O)OR^{12}$, —$NR^7S(O)_jR^{14}$, —$C(O)R^{11}$, —$C(S)R^{11}$, —$C(O)OR^{12}$, —$OC(O)R^{11}$, —$SO_2NR^1R^7$, —$S(O)_jR^{11}$, —CH=$NOR^{14}$, —$(CR^1R^2)_jS(O)_jR^{11}$, -$Z^2$-$(CR^1R^2)_n(C_6-C_{10}$ aryl), -$Z^2$-$(CR^1R^2)_n(C_6-C_{10}$ heteroaryl), or -$Z^2$-$(CR^1R^2)_n$(4- to 10-membered heterocyclic); wherein $Z^2$ is O, or —$(CR^1R^2)_n$; wherein the alkyl, alkenyl, alkynyl, aryl, heteroaryl and heterocyclic moieties of the foregoing $R^6$ groups are optionally substituted with 1 to 3 substituents independently selected from halo, cyano, nitro, trifluoromethyl, trifluoromethoxy, azido, —$OR^{12}$, —$C(O)R^{12}$, —$C(O)OR^{12}$, —$OC(O)R^{12}$, —$NR^{13}C(O)R^{12}$, —$C(O)NR^1R^{13}$, —$(CR^1R^2)_nNR^1R^{13}$, and —$NR^{13}OR^{12}$, $C_1-C_6$ alkyl, $C_2-C_6$ alkenyl, $C_2-C_6$ alkynyl, —$(CR^1R^2)_t(C_6-C_{10}$ aryl), and —$(CR^1R^2)_t$(4 to 10 membered heterocyclic); wherein each t is independently an integer from 0 to 5;

each $R^7$ is independently H, $(C_1-C_6)$alkyl, $(C_3-C_8)$cycloalkyl, —$C(O)R^{11}$, —$C(S)R^{11}$, —$(CR^1R^2)_nO(C_1-C_6$ alkyl), —$(CR^1R^2)_nS(O)_j(C_1-C_6$ alkyl), —$(CR^1R^2)_rC(O)R^{11}$, —$(CR^1R^2)_nR^{11}$ or —$SO_2R^{11}$; wherein each v is independently an integer from 2 to 5;

each $R^8$ is independently $(C_1-C_6)$alkyl, $(C_2-C_6)$alkenyl, $(C_2-C_6)$alkynyl, $(C_3-C_8)$cycloalkyl, $(C_1-C_6)$alkoxy, $(C_1-C_6)$alkylthio, hydroxy$(C_1-C_6)$alkyl, trifluoromethyl, trifluoromethyl$(C_2-C_6)$alkyl, trifluoromethoxy, trifluoro$(C_2-C_6)$alkoxy, —$(CR^1R^2)_nO(C_1-C_6$ alkyl), —$(CR^1R^2)_rS(O)_j(C_1-C_6$ alkyl), halo, hydroxy, cyano, nitro, azido, amino, —$(CR^1R^2)_nNR^1R^7$, —$C(O)NR^1R^7$, —$NR^1C(O)R^{11}$, —$NR^1OR^2$, —$NR^1C(O)OR^{12}$, —$NR^1S(O)_jR^{14}$, —$C(O)R^{11}$, —$C(S)R^{11}$, —$C(O)OR^{12}$, —$OC(O)R^{11}$, —$SO_2NR^1R^7$, —CH=$NOR^{14}$, —$S(O)_jR^1$, or —$(CR^1R^2)_rS(O)_jR^1$, wherein the alkyl, alkenyl and alkynyl moieties of the foregoing $R^8$ groups are optionally substituted with 1 to 3 substituents independently selected from halo, cyano, nitro, trifluoromethyl, trifluoromethoxy, azido, —$OR^{12}$, —$C(O)R^{12}$, —$C(O)OR^{12}$, —$OC(O)R^{12}$, —$NR^7C(O)R^{12}$, —$C(O)NR^1R^{13}$, —$NR^1R^{13}$, and —$NR^{13}OR^{12}$, $C_1-C_6$ alkyl, $C_2-C_6$ alkenyl, $C_2-C_6$ alkynyl, —$(CR^1R^2)_t(C_6-C_{10}$ aryl), and —$(CR^1R^2)_t$(4 to 10 membered heterocyclic);

$R^9$ is a fused-ring bicyclic, bridged bicyclic or spirobicylic group, wherein each ring in the bicyclic group is saturated or unsaturated or aromatic, wherein each ring in the bicyclic group optionally contains up to three heteroatoms selected from N, O, and S, and wherein each ring in the bicyclic group is optionally substituted on up to four atoms, wherein any optional carbon substituent is independently $R^{10}$, wherein any sp$^3$-hybridized nitrogen is optionally substituted with $R^7$; and provided that in $R^9$ the ring distal to the pyridopyrimidine of formula 1 does not comprise methylenedioxy or ethylenedioxy; or $R^9$ is azetidinyl substituted on one carbon with $R^{10}$;

each $R^{10}$ is independently $(C_1-C_6)$alkyl, $(C_2-C_6)$alkenyl, $(C_2-C_6)$alkynyl, $(C_3-C_8)$cycloalkyl, $(C_1-C_6)$alkoxy, $(C_1-C_6)$alkylthio, -hydroxy$(C_1-C_6)$alkyl, trifluoromethyl, trifluoromethyl$(C_2-C_6)$alkyl, trifluoromethoxy, trifluoro$(C_2-C_6)$alkoxy, —$(CR^1R^2)_nO(C_1-C_6$ alkyl), —$(CR^1R^2)_nS(O)_j(C_1-C_6$ alkyl), halo, hydroxy, cyano, nitro, azido, amino, —$(CR^1R^2)_nNR^1R^7$, —$C(O)NR^1R^7$, —$NR^7C(O)R^{11}$, —$NR^7OR^{14}$, —$NR^7C(O)OR^{12}$, —$NR^7S(O)_jR^{14}$, —$C(O)R^{11}$, —$C(S)R^{11}$, —$C(O)OR^{12}$, —$OC(O)R^{11}$, —$SO_2NR^1R^7$, —$S(O)_jR^{11}$, —CH=$NOR^{14}$, —$(CR^1R^2)_nS(O)_jR^{11}$, -$Z^2$-$(CR^1R^2)_n(C_6-C_{10}$ aryl), -$Z^2$-$(CR^1R^2)_n(C_6-C_{10}$ heteroaryl), or -$Z^2$-$(CR^1R^2)_n$(4- to 10-membered heterocyclic), wherein $Z^2$ is O, or —$(CR^1R^2)_n$—; wherein the alkyl, alkenyl, alkynyl, aryl, heteroaryl and heterocyclic moieties of the foregoing $R^{10}$ groups are optionally substituted with 1 to 3 substituents independently selected from halo, cyano, nitro, trifluoromethyl, trifluoromethoxy, azido, —$OR^{12}$, —$C(O)R^{12}$, —$C(O)OR^{12}$, —$OC(O)R^{12}$, —$NR^{13}C(O)R^{12}$, —$C(O)NR^1R^{13}$, —$(CR^1R^2)_nNR^1R^{13}$, and —$NR^7OR^{14}$, $C_1-C_6$ alkyl, $C_2-C_6$ alkenyl, $C_2-C_6$ alkynyl, —$(CR^1R^2)_t(C_6-C_{10}$ aryl), and —$(CR^1R^2)_t$(4 to 10 membered heterocyclic), wherein t is an integer from 0 to 5;

each $R^{11}$ is independently H, $(C_1-C_6)$alkyl, $(C_3-C_8)$cycloalkyl, -hydroxy$(C_2-C_6)$alkyl, trifluoromethyl, trifluoro$(C_2-C_6)$alkyl, —$(CR^1R^2)_nO(C_1-C_6$ alkyl), —$(CR^1R^2)_nS(O)_j(C_1-C_6$ alkyl), —$(CR^1R^2)_nNR^1R^{13}$, —$(CR^1R^2)_rC(O)NR^1R^{13}$, —$(CR^1R^2)_rC(O)R^{12}$, —$(CR^1R^2)_rC(S)R^{12}$, —$(CR^1R^2)_rC(O)OR^{12}$, —$(CR^1R^2)_rS(O)_jR^{12}$, —$(CR^1R^2)_n$—$(C_6-C_{10}$aryl), —$(CR^1R^2)_n$—$(C_6-C_{10}$heteroaryl), —$(CR^1R^2)_n$—(4 to 10 membered heterocyclic), wherein the alkyl, aryl, heteroaryl and heterocyclic moieties of the foregoing $R^{11}$ groups are optionally substituted with 1 to 3 substituents independently selected from halo, cyano, nitro, trifluoromethyl, trifluoromethoxy, azido, —$OR^{12}$, —$C(O)R^{12}$, —$C(O)OR^{12}$, —$OC(O)R^{12}$, —$NR^{13}C(O)R^{12}$, —$C(O)NR^1R^{13}$, —$NR^1R^{13}$, —$NR^{13}OR^{14}$, $C_1-C_6$ alkyl, $C_2-C_6$ alkenyl, $C_2-C_6$ alkynyl, —$(CR^1R^2)_t(C_6-C_{10}$ aryl), and —$(CR^1R^2)_t$(4 to 10 membered heterocyclic), wherein t is an integer from 0 to 5;

each $R^{12}$ is independently H, $(C_1-C_6)$alkyl, $(C_3-C_8)$cycloalkyl, -hydroxy$(C_2-C_6)$alkyl, trifluoromethyl, trifluoro$(C_2-C_6)$alkyl, —$(CR^1R^2)_n(C_1-C_6$ alkyl), —$(CR^1R^2)_nO(C_1-C_6$ alkyl), —$(CR^1R^2)_rS(O)_j(C_1-C_6$ alkyl), —$(CR^1R^2)_rNR^1R^{14}$, —$(CR^1R^2)_n$—$(C_6-C_{10}$aryl), —$(CR^1R^2)_n$—$(C_6-C_{10}$heteroaryl), —$(CR^1R^2)_n$-(4 to 10 membered heterocyclic), wherein the alkyl, aryl, heteroaryl and heterocyclic moieties of the foregoing $R^{12}$ groups are optionally substituted with 1 to 3 substituents independently selected from halo, cyano, nitro, trifluoromethyl, trifluoromethoxy, azido, —$OR^{14}$, —$C(O)R^{14}$, —$C(O)OR^{1}$, —$OC(O)R^{14}$, —$NR^{2}C(O)R^{14}$, —$C(O)NR^{1}R^{14}$, —$NR^{1}R^{14}$, —$NR^{2}OR^{1}$, $C_{1}$–$C_{6}$ alkyl, $C_{2}$–$C_{6}$ alkenyl, $C_{2}$–$C_{6}$ alkynyl, —$(CR^{1}R^{2})_{t}$ ($C_{6}$–$C_{10}$ aryl), and —$(CR^{1}R^{2})_{t}$(4 to 10 membered heterocyclic), wherein t is an integer from 0 to 5;

each $R^{13}$ is independently H, $(C_{1}$–$C_{6})$alkyl, $(C_{3}$–$C_{8})$ cycloalkyl, —$C(O)R^{14}$, —$C(S)R^{14}$, —$(CR^{1}R^{2})_{v}O(C_{1}$–$C_{6}$ alkyl), —$(CR^{1}R^{2})_{v}S(C_{1}$–$C_{6}$ alkyl), —$(CR^{1}R^{2})_{v}C(O)R^{14}$, —$(CR^{1}R^{2})_{n}R^{14}$, or —$SO_{2}R^{14}$; wherein v is an integer from 2 to 5;

each $R^{14}$ is independently H, $(C_{1}$–$C_{6})$alkyl, $(C_{3}$–$C_{8})$ cycloalkyl, trifluoromethyl, trifluoromethyl$(C_{2}$–$C_{6})$alkyl, —$(CR^{1}R^{2})_{n}(C_{6}$–$C_{10}$ aryl), —$(CR^{1}R^{2})_{n}(C_{6}$–$C_{10}$ heteroaryl), or —$(CR^{1}R^{2})_{n}$(4- to 10-membered heterocyclic), wherein the alkyl, aryl, heteroaryl and heterocyclic moieties of the foregoing $R^{14}$ groups are optionally substituted with 1 to 3 substituents independently selected from $C_{1}$–$C_{6}$ alkyl, $C_{1}$–$C_{6}$ alkoxy, amino, hydroxy, halo, cyano, nitro, trifluoromethyl, trifluoromethoxy;

and wherein any of the above substituents $R^{1}$ through $R^{14}$ comprising a $CH_{3}$ (methyl), $CH_{2}$ (methylene), or CH (methine) group which is not substituted with halogen, SO or $SO_{2}$, or attached to a N, O or S atom, optionally bears on said methyl, methylene or methine group a substituent selected from hydroxy, halo, $R^{1}$, —$OR^{1}$, —$SR^{1}$ and —$NR^{1}R^{2}$;

provided that in $R^{4}$, $R^{5}$ and any ring in $R^{9}$, two O atoms, two $S(O)_{j}$ moieties, an O atom and a $S(O)_{j}$ moiety, an N atom and an S atom, or an N atom and an O atom are not attached directly to each other within said ring.

In one embodiment, $R^{9}$ is a bridged bicyclic ring optionally substituted with from one to three $R^{10}$ groups. In a further embodiment, $R^{9}$ is a heterobicyclic group optionally substituted with from one to three $R^{10}$ groups. In a preferred embodiment, $R^{9}$ is an azabicyclic group containing 5–9 atoms attached to the pyridopyrimidine ring of formula 1 through a nitrogen atom, optionally substituted with from one to three $R^{10}$ groups. In a more preferred embodiment, $R^{9}$ is azabicycloalkyl containing from 5 to 9 atoms, optionally substituted with from one to three $R^{10}$ groups. In a particularly preferred embodiment, $R^{9}$ is azabicyclo[3.1.0]hexyl optionally substituted with from one to three $R^{10}$ groups. In another, separate embodiment, $R^{9}$ is azetidinyl substituted with one $R^{10}$ at the carbon β to the azetidinyl nitrogen. Where $R^{9}$ is azetidinyl, the azetidinyl is preferably attached to the pyridopyrimidine through the nitrogen atom. Where $R^{9}$ is azetidinyl linked to the pyridopyrimidine via a carbon atom, the azetidinyl nitrogen may be substituted with $R^{7}$.

In another embodiment, m is 0 and $R^{4}$ is phenyl optionally substituted on one atom with -$Z^{1}R^{5}$, optionally substituted on one other atom with $R^{6}$, and optionally substituted on up to three other atoms independently with $R^{8}$. In a preferred embodiment, $R^{4}$ is phenyl substituted on one atom with -$Z^{1}R^{5}$ and optionally substituted on one other atom with $R^{6}$. In a more preferred embodiment, $Z^{1}$ is oxygen. In a more preferred embodiment, $R^{9}$ is an azabicyclic group containing 5–9 atoms attached to the pyridopyrimidine ring of formula 1 through a nitrogen atom, wherein the $R^{9}$ is optionally substituted with from one to three $R^{10}$ groups.

In another embodiment, $R^{5}$ is phenyl, pyridin-2-yl or pyridin-3-yl, wherein the phenyl, pyridin-2-yl or pyridin-3-yl is optionally substituted on up to three atoms independently with $R^{8}$. In a preferred embodiment, $R^{9}$ is azabicycloalkyl containing from 5 to 9 atoms, optionally substituted with from one to three $R^{10}$ groups. In another preferred embodiment, each $R^{6}$ is independently $(C_{1}$–$C_{3})$alkyl, $(C_{1}$–$C_{3})$alkenyl, $(C_{1}$–$C_{3})$alkynyl, $(C_{1}$–$C_{3})$alkoxy, $(C_{1}$–$C_{3})$ alkylthio, trifluoromethyl, trifluoromethoxy, halo, cyano, nitro, azido or amino. In another preferred embodiment, each $R^{8}$ is independently $(C_{1}$–$C_{3})$alkyl, $(C_{1}$–$C_{3})$alkenyl, $(C_{1}$–$C_{3})$alkynyl, $(C_{1}$–$C_{3})$alkoxy, $(C_{1}$–$C_{3})$alkylthio, trifluoromethyl, trifluoromethoxy or halo. In another preferred embodiment, $R^{9}$ is azabicyclo[3.1.0]hexyl substituted with one $R^{10}$, wherein $R^{10}$ is $(C_{1}$–$C_{6})$alkyl, $(C_{1}$–$C_{6})$alkoxy, $(C_{1}$–$C_{6})$alkylthio, trifluoromethyl, trifluoromethoxy, -hydroxy$(C_{1}$–$C_{6})$alkyl, —$(CR^{1}R^{2})_{n}O(C_{1}$–$C_{6}$ alkyl), halo, amino, —$NR^{7}C(O)R^{11}$, —$NR^{7}S(O)_{2}R^{14}$, —$SO_{2}NR^{1}R^{7}$, —$S(O)_{j}R^{11}$, or —$(CR^{1}R^{2})_{n}S(O)_{j}R^{11}$.

In a particularly preferred embodiment, $R^{5}$ is phenyl optionally substituted on up to three atoms independently with $R^{8}$. In particularly preferred embodiments, the compound of formula 1 is selected from:

{3-[4-(3-Methyl-4-phenoxy-phenylamino)-pyrido[3,4-d] pyrimidin-6-yl]-3-aza-bicyclo[3.1.0]hex-6-yl}-methanol;

[6-(6-Dimethylamino-3-aza-bicyclo[3.1.0]hex-3-yl)-pyrido[3,4-d]pyrimidin-4-yl]-(3-methyl-4-phenoxy-phenyl)-amine;

{3-[4-(3-Methoxy-4-phenoxy-phenylamino)-pyrido[3,4-d]pyrimidin-6-yl]-3-aza-bicyclo[3.1.0]hex-6-yl}-methanol; and

[6-(6-Amino-3-aza-bicyclo[3.1.0]hex-3-yl)-pyrido[3,4-d]pyrimidin-4-yl]-(3-methyl-4-phenoxy-phenyl)-amine.

In another particularly preferred embodiment, $R^{10}$ is —$NR^{7}C(O)R^{11}$. In particularly preferred embodiments, the compound of formula 1 is selected from:

N-{3-[4-(3-Methyl-4-phenoxy-phenylamino)-pyrido[3,4-d]pyrimidin-6-yl]-3-aza-bicyclo[3.1.0]hex-6-yl}-acetamide; and Cyclopropanecarboxylic acid {3-[4-(3-methyl-4-phenoxy-phenylamino)-pyrido[3,4-d]pyrimidin-6-yl]-3-aza-bicyclo[3.1.0]hex-6-yl}-amide.

In another particularly preferred embodiment, $R^{5}$ is pyridin-3-yl optionally substituted on up to three atoms independently with $R^{8}$. In particularly preferred embodiments, the compound of formula 1 is selected from:

[6-(6-Amino-3-aza-bicyclo[3.1.0]hex-3-yl)-pyrido[3,4-d]pyrimidin-4-yl]-[3-methyl-4-(pyridin-3-yloxy)-phenyl]-amine;

[6-(6-Amino-3-aza-bicyclo[3.1.0]hex-3-yl)-pyrido[3,4-d]pyrimidin-4-yl]-[3-(pyridin-3-yloxy)-phenyl]-amine;

[6-(6-Amino-3-aza-bicyclo[3.1.0]hex-3-yl)-pyrido[3,4-d]pyrimidin-4-yl]-[3-methyl-4-(6-methyl-pyridin-3-yloxy)-phenyl]-amine;

N-(3-{4-[3-Methyl-4-(pyridin-3-yloxy)-phenylamino]-pyrido[3,4-d]pyrimidin-6-yl}-3-aza-bicyclo[3.1.0]hex-6-yl)-methanesulfonamide; and N-(3-{4-[3-Methyl-4-(6-methyl-pyridin-3-yloxy)-phenylamino]-pyrido[3,4-d]pyrimidin-6-yl}-3-aza-bicyclo [3.1.0]hex-6-yl)-methanesulfonamide.

In another particularly preferred embodiment, $R^{10}$ is —$NR^{7}C(O)R^{11}$. In particularly preferred embodiments, the compound of formula 1 is selected from:

N-(3-{4-[3-methyl-4-(pyridin-3-yloxy)-phenylamino]-pyrido[3,4-d]pyrimidin-6-yl}-3-aza-bicyclo[3.1.0]hex-6-yl)-acetamide;

2-Methoxy-N-(3-{4-[3-methyl-4-(pyridin-3-yloxy)-phenylamino]-pyrido[3,4-d]pyrimidin-6-yl}-3-aza-bicyclo [3.1.0]hex-6-yl)-acetamide;

Cyclopropanecarboxylic acid (3-{4-[3-methyl-4-(pyridin-3-yloxy)-phenylamino]-pyrido[3,4-d]pyrimidin-6-yl}-3-aza-bicyclo[3.1.0]hex-6-yl)-amide;

Thiophene-2-carboxylic acid (3-{4-[3-methyl-4-(pyridin-3-yloxy)-phenylamino]-pyrido[3,4-d]pyrimidin-6-yl}-3-aza-bicyclo[3.1.0]hex-6-yl)-amide;

N-(3-{4-[3-Methyl-4-(pyridin-3-yloxy)-phenylamino]-pyrido[3,4-d]pyrimidin-6-yl}-3-aza-bicyclo[3.1.0]hex-6-yl)-2-methylsulfanyl-acetamide;

N-(3-{4-[3-Chloro-4-(pyridin-3-yloxy)-phenylamino]-pyrido[3,4-d]pyrimidin-6-yl}-3-aza-bicyclo[3.1.0]hex-6-yl)-acetamide;

Thiophene-2-carboxylic acid (3-{4-[3-methyl-4-(6-methyl-pyridin-3-yloxy)-phenylamino]-pyrido[3,4-d]pyrimidin-6-yl}-3-aza-bicyclo[3.1.0]hex-6-yl)-amide;

N-(3-{4-[3-Methyl-4-(6-methyl-pyridin-3-yloxy)-phenylamino]-pyrido[3,4-d]pyrimidin-6-yl}-3-aza-bicyclo[3.1.0]hex-6-yl)-2-methylsulfanyl-acetamide;

2-Methoxy-N-(3-{4-[3-methyl-4-(6-methyl-pyridin-3-yloxy)-phenylamino]-pyrido[3,4-d]pyrimidin-6-yl}-3-aza-bicyclo[3.1.0]hex-6-yl)-acetamide; and N-(3-{4-[3-Methyl-4-(6-methyl-pyridin-3-yloxy)-phenylamino]-pyrido[3,4-d]pyrimidin-6-yl}-3-aza-bicyclo[3.1.0]hex-6-yl)-acetamide.

In other particularly preferred embodiments, the compound of formula 1 is selected from:

[6-(3-Methoxy-azetidin-1-yl)-pyrido[3,4-d]pyrimidin-4-yl]-[3-methyl-4-(6-methyl-pyridin-3-yloxy)-phenyl]-amine;

(1-{4-[3-Methyl-4-(6-methyl-pyridin-3-yloxy)-phenylamino]-pyrido[3,4-d]pyrimidin-6-yl}-azetidin-3-yl)-carbamic acid tert-butyl ester;

2-Methoxy-N-(1-{4-[3-methyl-4-(6-methyl-pyridin-3-yloxy)-phenylamino]-pyrido[3,4-d]pyrimidin-6-yl}-azetidin-3-yl)-acetamide;

[6-(3-Methanesulfonyl-azetidin-1-yl)-pyrido[3,4-d]pyrimidin-4-yl]-[3-methyl-4-(6-methyl-pyridin-3-yloxy)-phenyl]-amine;

[6-(6-Amino-3-aza-bicyclo[3.1.0]hex-3-yl)-pyrido[3,4-d]pyrimidin-4-yl]-[4-(2-fluoro-phenoxy)-3-methyl-phenyl]-amine;

[4-(2-Fluoro-phenoxy)-3-methyl-phenyl]-[6-(hexahydro-pyrrolo[3,4-c]pyrrol-2-yl)-pyrido[3,4-d]pyrimidin-4-yl]-amine;

[6-(6-Amino-3-aza-bicyclo[3.1.0]hex-3-yl)-pyrido[3,4-d]pyrimidin-4-yl]-(3-chloro-4-phenoxy-phenyl)-amine;

[6-(6-Amino-3-aza-bicyclo[3.1.0]hex-3-yl)-pyrido[3,4-d]pyrimidin-4-yl]-[4-(3-fluoro-phenoxy)-3-methoxy-phenyl]-amine; and

[6-(6-Amino-3-aza-bicyclo[3.1.0]hex-3-yl)-pyrido[3,4-d]pyrimidin-4-yl]-[4-(2,6-difluoro-phenoxy)-3-methyl-phenyl]-amine.

It is to be understood that the term "compound of formula 1" as used in this application includes the compound of formula 1 as defined above in all its embodiments, preferred embodiments, more preferred embodiments, still more preferred embodiments and particularly preferred embodiments.

It is also to be understood that the term "nitrogen substituent" as used in this application means a group attached to a $sp^3$-hybridized nitrogen atom through a covalent bond, wherein the nitrogen with its substituent comprises a secondary or tertiary amine.

The term "halo", as used herein, unless otherwise indicated, means fluoro, chloro, bromo or iodo. Preferred halo groups are fluoro, chloro and bromo.

The term "alkyl", as used herein, unless otherwise indicated, means straight, and branched monovalent hydrocarbon radicals. For example, a $C_1$–$C_6$ alkyl includes, but is not limited to, an n-butyl radical and a tert-butyl radical. It is understood that for cyclic moieties at least 3 carbon atoms must be present in said alkyl group. The term "alkylene" as used herein, unless otherwise indicated, means divalent hydrocarbon radicals which are straight or branched, e.g., methylene or —$CH_2$—.

The term "cycloalkyl", as used herein, unless otherwise indicated includes saturated cyclic alkyl groups as well as non-aromatic cyclic alkyl groups comprising one or more points of unsaturation, i.e. one or more carbon-carbon double bonds. Examples of cycloalkyl groups include cyclopropyl, cyclohexyl and cyclohexenyl.

The term "alkenyl", as used herein, unless otherwise indicated, means straight and branched monovalent hydrocarbon radicals which comprise at least one carbon-carbon double bond. It is understood that at least two carbon atoms must be present for each carbon-carbon double bond in such moieties.

The term "alkynyl", as used herein, unless otherwise indicated, means straight and branched monovalent hydrocarbon radicals which comprise at least one carbon-carbon triple bond. It is understood that at least two carbon atoms must be present for each carbon-carbon triple bond in such moieties.

The term "haloalkyl", as used herein, unless otherwise indicated, means alkyl groups, wherein "alkyl" is as defined above, substituted with one or more halo groups, on one or more carbon atoms. Preferably, the haloalkyl comprises 1 to 3 halo groups, such as a hydrocarbon comprising a trifluoromethyl or a trichloromethyl group, or a monohalosubstituted hydrocarbon.

The term "alkoxy", as used herein, unless otherwise indicated, means —O-alkyl groups wherein "alkyl" is as defined above. Examples of alkoxy groups include, but are not limited to, methoxy, ethoxy and propoxy.

The term "haloalkoxy", as used herein, unless otherwise indicated, means an —O-haloalkyl group wherein "haloalkyl" is as defined above. An example of a haloalkoxy group is trifluoromethoxy.

The term "aryl", as used herein, unless otherwise indicated, means an organic radical derived from an aromatic hydrocarbon by removal of one hydrogen, such as phenyl, benzyl or naphthyl. Aryl is preferably phenyl.

The terms "heterocyclyl" and "heterocyclic", as used herein, unless otherwise indicated, mean non-aromatic (saturated or unsaturated) monocyclic and multicyclic groups containing one or more heteroatoms each selected from O, S and N, wherein each ring of a heterocyclic group has from 3 to 8 atoms. Preferably, heterocyclic groups of this invention are monocyclic or bicyclic.

Monocyclic heterocyclic groups include rings having only 4 atoms; preferably, monocyclic heterocyclic groups contain from 4 to 8 members, and more preferably, from 4 to 6 members. An example of a 4-membered heterocyclic group is azetidinyl (derived from azetidine), an example of a 5-membered heterocyclic group is imidazolidinyl, and an example of a 6-membered heterocyclic group is piperidinyl. Other examples of monocyclic heterocyclic groups are pyrrolidinyl, tetrahydrofuranyl, tetrahydrothiophenyl, tetrahydropyranyl, tetrahydrothiopyranyl, morpholino, thiomorpholino, thioxanyl, piperazinyl, 1,2,3,6-tetrahydropyridinyl, pyrrolinyl, 2H-pyranyl, 4H-pyranyl, 1,4-dioxanyl, 1,3-dioxolanyl, 1,4-dithianyl, pyrazolinyl, pyrazolidinyl, dihydropyranyl, dihydrothiophenyl, dihydrofuranyl and imidazolinyl. Other examples of monocyclic heterocyclic groups include azacycloheptane and azacyclooctane. Preferred monocyclic heterocyclic groups are azetidinyl, pyrrolidinyl, imidazolidinyl and piperidinyl.

Bicyclic heterocyclic groups may also be referred to herein as "heterobicyclic" or "heterobicyclyl", both of which as used herein mean heterocyclic groups containing two rings, and encompass fused-ring bicyclic, bridged bicyclic and spiro-bicyclic groups. Heterobicyclic groups preferably contain from 5 to 12 members, more preferably, from 6 to 10 members. Preferably, each ring of a heterobicyclic group contains from 3 to 6 members. An example of a heterobicyclic group is 1,4-dioxaspiro[4.5]decyl. In this application, the term "bridged" when referring to any bicyclic group means that the two rings share at least two common atoms; the shared atoms are known in the art as "bridgehead" atoms. Spiro bicyclic groups, in contrast, are bicyclic groups whose two rings share only a single bridgehead atom.

Preferred among the heterobicyclic groups of this invention are azabicyclic groups. The terms "azabicyclic", "azabicyclyl", and the like, as used herein, unless otherwise indicated, mean a heterobicyclic group as defined above wherein at least one member of at least one ring is a nitrogen atom. An example of an azabicyclic group is quinuclidinyl. Preferred azabicyclic groups are bridged azabicycloalkyl groups. Some examples of bridged azabicycloalkyl groups include 2-azabicyclo[2.1.0]pentyl, 3-azabicyclo[3.1.0]hexyl, 3-azabicyclo[4.1.0]heptyl, 3-azabicyclo[3.3.0]octyl, 2-aza-5-thiabicyclo[2.2.1]heptyl, 8-azabicyclo[3.2.1]octyl (nortropanyl), 3-azabicyclo[3.2.2]nonyl. Other azabicycloalkyl groups include azaspiro groups, some examples of which include 8-azaspiro[4.5]decyl, 8-azaspiro[4.5]dec-2-enyl, 3-azaspiro[5.5]undecyl and 3,9-diazaspiro[5.5]undecyl groups. Azabicyclic groups may also include groups having one or more oxo moieties, e.g., 2-aza-5-oxabicyclo[2.2.1]heptyl, 2-azabicyclo[2.2.1]hept-3-oxo-5-enyl (derived from 2-azabicyclo[2.2.1]hept-5-en-3-one). Preferred among the azabicyclic groups are those containing one or two nitrogen atoms, and more preferred are those azabicyclic groups wherein at least one nitrogen atom is $sp^3$-hybridized, i.e., capable of forming covalent bonds with three other atoms. More preferred azabicyclic groups include the azabicycloalkyl groups 3-azabicyclo[3.1.0]hexyl, 3-azabicyclo[4.1.0]heptyl, 3-azabicyclo[3.2.0]heptyl, 8-azabicyclo[3.2.1]octyl (nortropanyl) and 3-azabicyclo[3.2.2]nonyl. Particularly preferred azabicycloalkyl groups are 3-azabicyclo[3.1.0]hexyl and 3-azabicyclo[3.2.0]heptyl.

The term "heteroaryl" as used herein means aromatic heterocyclic groups comprising from 5 to 12 atoms and containing one or more heteroatoms each selected from O, S and N, wherein each ring of the heteroaryl group contains from 3 to 8 atoms. Heteroaryl groups of this invention unless otherwise indicated may contain one ring or more than one ring, i.e., they may be monocyclic or multicyclic, for example bicyclic, so long as at least one ring in a multicyclic group is aromatic. Preferably, heteroaryl groups of this invention are monocyclic or bicyclic. Preferably, each ring of a heteroaryl group contains one or two heteroatoms. Monocyclic heteroaryl groups preferably contain from 5 to 8 members, more preferably, 5 or 6 members. Preferably, multicyclic heteroaryl groups are bicyclic; bicyclic heteroaryl groups preferably contain 9 or 10 members. Some examples of heteroaryl groups are pyridinyl, imidazolyl, pyrimidinyl, pyrazolyl, triazolyl, pyrazinyl, tetrazolyl, furyl, thiophenyl (also sometimes identified as "thienyl"), isoxazolyl, thiazolyl, oxazolyl, isothiazolyl, pyrrolyl, quinolinyl, isoquinolinyl, indolyl, 3H-indolyl, indolinyl, benzimidazolyl, benzofuranyl, cinnolinyl, indazolyl, indolizinyl, phthalazinyl, pyridazinyl, triazinyl, isoindolyl, purinyl, oxadiazolyl, thiadiazolyl, furazanyl (i.e., 2,5-diaza-furanyl), benzofurazanyl, benzothiophenyl, benzothiazolyl, benzisothiazolyl, benzoxazolyl, pteridinyl, benzothiadiazine, benzothiazinyl, 2H-1-benzopyranyl, chromanyl, benzoxazolyl, quinazolinyl, quinoxalinyl, naphthyridinyl, and furopyridinyl.

The foregoing heterocyclic and heteroaryl groups may be C-attached or N-attached where such is possible. For instance, pyrrolyl may be pyrrol-1-yl (N-attached) or pyrrol-3-yl (C-attached). The heterocyclic groups of this invention also include ring systems substituted with one or more oxo moieties. Preferred among the heteroaryl groups are thiophenyl and pyridinyl, i.e., pyridin-2-yl or pyridin-3-yl.

The term "pharmaceutically acceptable salt(s)", as used herein, unless otherwise indicated, includes salts of acidic or basic groups that may be present in the compounds of formula 1. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature, are capable of forming base salts with various pharmacologically acceptable cations. Examples of such salts include the alkali metal or alkaline earth metal salts and particularly, the sodium and potassium salts.

This invention also encompasses pharmaceutical compositions containing, and methods of treating proliferative disorders or abnormal cell growth through administering, prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

In certain combination therapies with other anti-cancer agents, such as those described below, the compound of formula 1 may further comprise a prodrug which comprises a compound of formula 1 in a hydrolyzable linkage to another anti-cancer agent. Di-ester linkages, for example, are particularly useful for this purpose, i.e., the prodrug is in the form $A^1$-C(O)O-$L^1$-O(O)C-$A^2$, wherein $A^1$ and $A^2$ are the two agents, $L^1$ is a linker such as a methylene or other ($C_1$–$C_6$) alkylene group (alone or further comprising a phenyl or benzyl group). See, e.g., U.S. Pat. No. 4,342,772—penicillins in di-ester linkages with β-lactamase inhibitors. Accordingly, a compound of formula 1 having an available carboxylic acid group provides just one convenient means of producing combination prodrugs of the compound of formula 1, which are encompassed by this invention. Typically, the acidic conditions of the gastrointestinal tract, or enzymes localized in the cells thereof cause the hydrolysis of the prodrug, releasing both agents.

Certain compounds of formula 1 may have asymmetric centers and therefore exist in different enantiomeric forms. All optical isomers and stereoisomers of the compounds of formula 1, and mixtures thereof, are considered to be within the scope of the invention. With respect to the compounds of formula 1, the invention includes the use of a racemate, one or more enantiomeric forms, one or more diastereomeric forms, or mixtures thereof. The compounds of formula 1 may also exist as tautomers, including, e.g., keto-enol tautomers. This invention relates to the use of all such tautomers and mixtures thereof.

The subject invention also relates to isotopically-labelled compounds of formula 1, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl, respectively. Compounds of the present invention and pharmaceutically acceptable salts of said compounds which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula 1 of this invention can generally be prepared by carrying out the procedures disclosed in the Schemes and/or in the Examples below, by substituting a readily available isotopically labelled reagent for a non-isotopically labelled reagent.

This invention also relates to a process for preparing a compound of formula 1, which comprises reacting a compound of formula 2

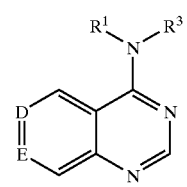

with $R^9$, wherein $R^9$ comprises an azetidinyl or azabicyclic group, in a polar solvent with heating, wherein either D is C—F or C—Cl and E is N, or D is N and E is C—F or C—Cl.

This invention relates to a pharmaceutical composition comprising a compound of formula 1, or a pharmaceutically acceptable salt or solvate or prodrug thereof, and a pharmaceutically acceptable carrier. In a preferred embodiment, the compound of formula 1 is a pharmaceutically acceptable salt thereof. In another preferred embodiment, the compound of formula 1 is a prodrug thereof. In still another preferred embodiment, the compound of formula 1 is a solvate thereof.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating, as "treating" is defined immediately above.

Patients that can be treated with compounds of the formula 1, as defined above, or pharmaceutically acceptable salts thereof, according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

Other examples of patients which may be treated with compounds of formula 1 or pharmaceutically acceptable salts of such compounds according to the methods of the invention include patients suffering from benign proliferative diseases such as psoriasis, benign prostatic hypertrophy or restenosis.

The invention also relates to a pharmaceutical composition for the treatment of a hyperproliferative disorder in a mammal which comprises a therapeutically effective amount of a compound of formula 1, (including those preferred, more preferred, still more preferred or particularly preferred compounds of formula 1, as defined above) or a pharmaceutically acceptable salt, prodrug or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, oesophageal, gynecological or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertrophy (BPH)). The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1, or a pharmaceutically acceptable salt, prodrug or hydrate thereof, and a pharmaceutically acceptable carrier. The invention also relates to a pharmaceutical composition for the prevention of blastocyte implantation in a mammal which comprises a therapeutically effective amount of a compound of formula 1, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of formula 1, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula 1, or a pharmaceutically acceptable salt, prodrug or hydrate thereof. In one embodiment, said method relates to the treatment of cancer such as brain, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., benign prostatic hypertrophy (BPH)). The invention also relates to a method for the treatment of a hyperproliferative disorder in a mammal which comprises administering to said mammal a therapeutically effective amount of a compound of formula 1, or a pharmaceutically acceptable salt, prodrug or hydrate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens. The invention also relates to a method of treating pancreatitis or kidney disease in a mammal which comprises administering to said mammal a therapeutically effective amount of a compound of formula 1, or a pharmaceutically acceptable salt, prodrug or hydrate thereof. The invention also relates to a method of preventing blastocyte implantation in a mammal which comprises administering to said mammal a therapeutically effective amount of a compound of formula 1, or a pharmaceutically acceptable salt, prodrug or hydrate thereof.

The invention also relates to a method of treating diseases related to vasculogenesis or angiogenesis in a mammal which comprises administering to said mammal an effective amount of a compound of formula 1, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer. Patients that can be treated with a compounds of formula 1, and the pharmaceutically acceptable salts, prodrugs and hydrates of said compounds, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a method of inhibiting abnormal cell growth in a mammal comprising administering to said mammal a therapeutically effective amount of a compound of formula 1, or a pharmaceutically acceptable salt, prodrug or solvate thereof. This invention also relates to a pharmaceutical composition for inhibiting abnormal cell growth in a mammal which comprises an amount of a compound of formula 1, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

This invention further relates to a method for inhibiting abnormal cell growth in a mammal which method comprises administering to the mammal an amount of a compound of formula 1, or a pharmaceutically acceptable salt or solvate or prodrug thereof, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula 1 can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula 1 or pharmaceutically acceptable salt, prodrug or solvate thereof, which amount is effective in sensitizing abnormal cells to treatment with radiation. The amount of the compound, salt, or solvate in this method can be determined according to the means for ascertaining effective amounts of such compounds described herein.

This invention also relates to a pharmaceutical composition for inhibiting abnormal cell growth in a mammal, including a human, comprising an amount of a compound of the formula 1 as defined above, or a pharmaceutically acceptable salt, prodrug or solvate thereof, that is effective in inhibiting farnesyl protein transferase, and a pharmaceutically acceptable carrier. This invention further relates to a pharmaceutical composition for inhibiting abnormal cell growth in a mammal comprising an amount of a compound of formula 1, or a pharmaceutically acceptable salt or solvate or prodrug thereof, that is effective in inhibiting abnormal cell growth, and a pharmaceutically acceptable carrier. This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of formula 1 and pharmaceutical compositions described herein. Examples of useful COX-II inhibitors include CELEBREX™ (celecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

(R) 3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide;

and pharmaceutically acceptable salts and solvates of all of the compounds described above.

Other anti-angiogenesis agents, including other COX-II inhibitors and other MMP inhibitors, can also be used in the present invention.

A compound of formula 1 can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and other erbB2 receptor inhibitors, such as organic molecules or antibodies that bind to the erbB2 receptor, for example, HERCEPTIN™ (Genentech, Inc. of South San Francisco, Calif. USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y, USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention. VEGF inhibitors, for example SU-5416 and SU-6668 (Sugen Inc. of South San Francisco, Calif., USA), can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein. ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The compound of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application No. 60/113,647 (filed Dec. 23, 1998) which is incorporated by reference in its entirety, however other CTLA4 antibodies can be used in the present invention.

The compounds of formula 1 and their pharmaceutically acceptable salts, prodrugs and solvates can each independently also furthermore be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The terms "abnormal cell growth" and "hyperproliferative disorder" are used interchangeably in this application. "Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restenosis. "Abnormal cell growth" also refers to and includes the abnormal growth of cells, both benign and malignant, resulting from activity of the enzyme farnesyl protein transferase. Any patient suffering from abnormal cell growth as defined above can be treated with compounds of the formula 1 according to the methods of this invention.

DETAILED DESCRIPTION OF THE INVENTION

The compounds of the present invention are readily prepared according to synthetic methods familiar to those skilled in the art. Some examples of the preparation of the compounds of the present invention are described below for illustrative purposes.

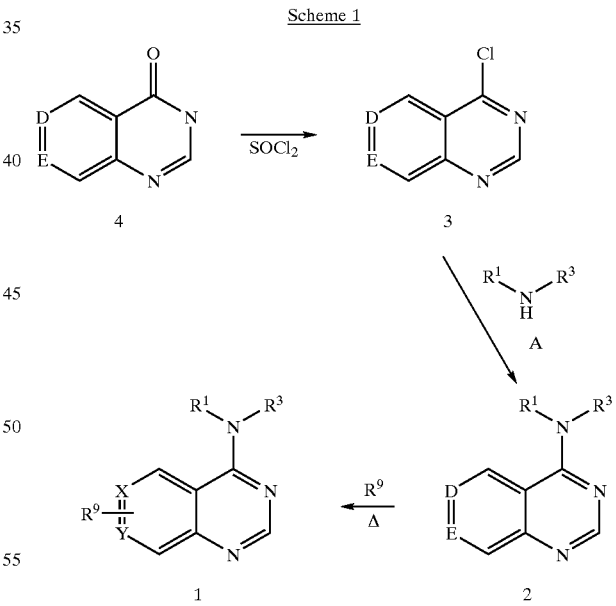

Scheme 1

The compounds of this invention as described herein, and represented in the above scheme for illustrative purposes by the compound of formula 1, may be readily prepared using methods well-known in the art. In the above Scheme, either D is C—F or C—Cl and E is N, or D is N and E is C—F or C—Cl, i.e., the process is the same regardless of whether the fluoro (or chloro) group is 6- or 7- on the pyridopyrimidine. The compounds of formula 3 are readily prepared by chlorination of a compound of formula 4, for example using an appropriate chlorinating reagent, preferably a thionyl, carbonyl or phosphoryl chloride, e.g., $SOCl_2$, $(COCl)_2$, or $PO(Cl)_3$.

Compounds of formula 2 are readily prepared by reacting an amine of formula A with a compound of formula 3, using methods which are well-known in the art; see Background of the invention for numerous references to such methods. The heteroaryloxyanilines of formula A may be prepared by methods known to those skilled in the art, such as, reduction of the corresponding nitro intermediates. Reduction of aromatic nitro groups may be performed by methods outlined in Brown, R. K., Nelson, N. A. J. Org. Chem. 1954, p. 5149; Yuste, R., Saldana, M, Walls, F., Tet. Lett. 1982, 23, 2, p. 147; or in WO 96/09294, referred to above. Appropriate heteroaryloxy nitrobenzene derivatives may be prepared from halo nitrobenzene precursors by nucleophilic displacement of the halide with an appropriate alcohol as described in Dinsmore, C. J. et. al., Bioorg. Med. Chem. Lett., 7, 10, 1997, 1345; Loupy, A. et. al., Synth. Commun., 20, 18, 1990, 2855; or Brunelle, D. J., Tet. Lett., 25, 32, 1984, 3383. Compounds of formula A in which $R^1$ is a $C_1$–$C_6$ alkyl group may be prepared by reductive amination of the parent aniline with $R^1CH(O)$.

Finally, compounds of formula 1 are readily prepared from compounds of formula 2, wherein $R^9$ comprises a secondary amine, by heating the compound of formula 2 and the amine, to yield the N-linked compound of formula 1, wherein $R^9$ is linked to the pyridopyrimidine through nitrogen. Compounds in which $R^9$ is carbon-linked are readily prepared by methods well-known in the art. In this case, for example, D is preferably C—I and E is N, or D is N and E is preferably C—I, and the pyridopyrimidine is reacted with an $R^9$ which comprises a bicyclic system which is a boronic acid derivative, i.e., $R^9$—$B(OH)_2$. The reaction is preferably catalyzed through the use of a palladium catalyst. The converse reaction, wherein the pyridopyrimidine is derivatized with boronic acid and $R^9$ is substituted with iodine, is also available.

The compounds of the present invention may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention. The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula 1. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The in vitro activity of the compounds of formula 1 may be determined by the following procedure. The c-erbB2 kinase assay is similar to that described previously in Schrang et. al. Anal. Biochem. 211, 1993, p233–239. Nunc MaxiSorp 96-well plates are coated by incubation overnight at 37° C. with 100 mL per well of 0.25 mg/mL Poly (Glu, Tyr) 4:1 (PGT) (Sigma Chemical Co., St. Louis, Mo.) in PBS (phosphate buffered saline). Excess PGT is removed by aspiration, and the plate is washed three times with wash buffer (0.1% Tween 20 in PBS). The kinase reaction is performed in 50 mL of 50 mM HEPES (pH 7.5) containing 125 mM sodium chloride, 10 mM magnesium chloride, 0.1 mM sodium orthovanadate, 1 mM ATP, 0.48 mg/mL (24 ng/well) c-erbB2 intracellular domain. The intracellular domain of the erbB2 tyrosine kinase (amino acids 674–1255) is expressed as a GST fusion protein in Baculovirus and purified by binding to and elution from glutathione-coated beads. The compound in DMSO (dimethylsulfoxide) is added to give a final DMSO concentration of about 2.5%. Phosphorylation was initiated by addition of ATP (adenosine triphosphate) and proceeded for 6 minutes at room temperature, with constant shaking. The kinase reaction is terminated by aspiration of the reaction mixture and subsequent washing with wash buffer (see above). Phosphorylated PGT is measured by 25 minutes of incubation with 50 mL per well HRP-conjugated PY54 (Oncogene Science Inc. Uniondale, N.Y.) antiphosphotyrosine antibody, diluted to 0.2 mg/mL in blocking buffer (3% BSA and 0.05% Tween 20 in PBS). Antibody is removed by aspiration, and the plate is washed 4 times with wash buffer. The colorimetric signal is developed by addition of TMB Microwell Peroxidase Substrate (Kirkegaard and Perry, Gaithersburg, Md.), 50 mL per well, and stopped by the addition of 0.09 M sulfuric acid, 50 mL per well. Phosphotyrosine is estimated by measurement of absorbance at 450 nm. The signal for controls is typically 0.6–1.2 absorbance units, with essentially no background in wells without the PGT substrate and is proportional to the time of incubation for 10 minutes. Inhibitors were identified by reduction of signal relative to wells without inhibitor and $IC_{50}$ values corresponding to the concentration of compound required for 50% inhibition are determined.

The activity of the compounds of formula 1, in vivo, can be determined by the amount of inhibition of tumor growth by a test compound relative to a control. The tumor growth inhibitory effects of various compounds are measured according to the method of Corbett T. H., et al., "Tumor Induction Relationships in Development of Transplantable Cancers of the Colon in Mice for Chemotherapy Assays, with a Note on Carcinogen Structure", Cancer Res., 35, 2434–2439 (1975) and Corbett T. H., et al., "A Mouse Colon-tumor Model for Experimental Therapy", Cancer Chemother. Rep. (Part 2)", 5, 169–186 (1975), with slight modifications. Tumors are induced in the left flank by subcutaneous (sc) injection of 1–5 million log phase cultured tumor cells (murine FRE-ErbB2 cells or human SK-OV3 ovarian carcinoma cells) suspended in 0.1 ml RPMI 1640 medium. After sufficient time has elapsed for the tumors to become palpable (100–150 mm3 in size/5–6 mm in diameter) the test animals (athymic female mice) are treated with test compound (formulated at a concentration of 10 to 15 mg/ml in 5 Gelucire) by the intraperitoneal (ip) or oral (po) route of administration once or twice daily for 7 to 10 consecutive days. In order to determine an anti-tumor effect, the tumor is measured in millimeters with a Vernier caliper across two diameters and the tumor size (mm3) is calculated using the formula: Tumor size (mm3)=(length×[width]2)/2, according to the methods of Geran, R. I., et al. "Protocols for Screening Chemical Agents and Natural Products Against Animal Tumors and Other Biological Systems", Third Edition, Cancer Chemother. Rep., 3, 1–104 (1972). Results are expressed as percent inhibition, according to the formula: Inhibition (%)=(TuW$_{control}$−TuW$_{test}$)/TuW$_{control}$×100%. The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration. The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumor substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes; biologicals, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations.

Where HPLC chromatography is referred to in the preparations and examples below, the general conditions used, unless otherwise indicated, are as follows. The column used is a ZORBAX™ RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 mL/minute.

EXAMPLE 1

Compound 1: [6-(6-Amino-3-aza-bicyclo[3.1.0]hex-3-yl)-pyrido[3,4-d]pyrimidin-4-yl]-[3-methyl-4-(pyridin-3-yloxy)-phenyl]-amine.

Part A. 4-Chloro-6-fluoro-pyrido[3,4-d]pyrimidine.

A slurry of 5.0 g (30.3 mmol) of 6-fluoro-3H-pyrido[3,4-d]pyrimidin-4-one and 21.0 mL of thionyl chloride was treated with 2.0 mL of dimethylformamide and the mixture was heated to reflux for 6 hours. The mixture was cooled and concentrated in vacuo. The dark solid was dissolved in methylene chloride and washed 2×50 mL with saturated sodium bicarbonate, 1×50 mL water, and 1×100 mL saturated sodium chloride. The organics were dried over sodium sulfate and concentrated to afford 5.56 g (100%) of the title compound. $^1$H NMR (d$_6$ DMSO): δ 8.75 (s, 1), 8.18 (s, 1), 7.64 (s, 1).

Part B. (6-Fluoro-pyrido[3,4-d]pyrimidin-4-yl)-[3-methyl-4-(pyridin-3-yloxy)-phenyl]-amine.

A solution of 2.78 g (15.1 mmol) of 4-chloro-6-fluoro-pyrido[3,4-d]pyrimidine and 3.03 g (15.1 mmol) of 3-methyl-4-(pyridin-3-yloxy)-phenylamine in 150 mL of 1:1 t-butanol/dichloroethane were heated to reflux for 1 hour. The mixture was allowed to cool to room temperature and diluted with chloroform. The organics were washed with 2×100 mL of saturated sodium bicarbonate, 1×50 mL of lithium chloride, 1×100 mL of water, and 1×100 ml of saturated sodium chloride. The solvent was dried over magnesium sulfate and evaporated. Recrystallization from methanol afforded 3.28 g (62%) of the title compound. $^1$H NMR (d$_6$ DMSO): 67 10.05 (s, 1), 8.90 (s, 1), 8.65 (s, 1), 8.28 (m, 2), 8.24 (s, 1), 7.81 (m, 1), 7.72 (m, 1), 7.36 (m, 1), 7.25 (m, 1), 7.02 (d, 1), 2.18 (s, 3).

Part C. (3-{4-[3-Methyl-4-(pyridin-3-yloxy)-phenylamino]-pyrido[3,4-d]pyrimidin-6-yl}-3-aza-bicyclo[3.1.0]hex-6-yl)-carbamic acid tert-butyl ester.

A solution of 2.71 g (7.83 mmol) of (6-fluoro-pyrido[3,4-d]pyrimidin-4-yl)-[3-methyl-4-(pyridin-3-yloxy)-phenyl]-amine and 31.0 g (156.5 mmol) of (3-aza-bicyclo[3.1.0]hex-6-yl)-carbamic acid tert-butyl ester in 20 mL of ethanol in a sealed tube was heated at 105° C. for 24 hours. The mixture was cooled to room temperature and diluted with chloroform. The organics were washed sequentially with 3×150 mL saturated sodium bicarbonate and 1×50 mL of saturated sodium chloride, dried over sodium sulfate and evaporated. Chromatography over silica gel, eluting with 5% methanol/chloroform afforded 1.79 g (43%) of the title compound. $^1$H NMR (CDCl$_3$): δ 8.93 (s, 1), 8.53 (s, 1), 8.33 (m, 2), 7.60 (m, 3), 7.21 (m, 2), 6.96 (d, 1), 6.24 (m, 1), 4.83 (m, 1), 3.81 (m, 2), 3.51 (m, 2), 3.47 (m, 1), 2.36 (m, 1), 2.26 (s, 3), 1.88 (m, 1).

Part D. [6-(6-Amino-3-aza-bicyclo[3.1.0]hex-3-yl)-pyrido[3,4-d]pyrimidin-4-yl]-[3-methyl-4-(pyridin-3-yloxy)-phenyl]-amine).

A sample (0.26 g, 0.49 mmol) of (3-{4-[3-Methyl-4-(pyridin-3-yloxy)-phenylamino]-pyrido[3,4-d]pyrimidin-6-yl}-3-aza-bicyclo[3.1.0]hex-6-yl)-carbamic acid tert-butyl ester was treated with 0.5 mL of trifluoroacetic acid and immediately concentrated in vacuo. The residue was dissolved in chloroform and washed with saturated sodium bicarbonate. The aqueous layer was back extracted several times with chloroform. The organics were dried over sodium sulfate and evaporated to afford 206 mg of the title compound. A pure sample was obtained by crystallization from methanol and isopropyl ether. $^1$H NMR (CDCl$_3$): δ 8.96 (s, 1), 8.53 (s, 1), 8.33 (m, 2), 7.65 (m, 1), 7.55 (m, 1), 7.21 (m, 2), 6.96 (d, 1), 615 (s, 1), 3.76 (d, 2), 3.54 (m, 2), 2.26 (s, 3), 2.24 (m, 1), 1.76 (m, 2). M.S. (m+1): 426. HPLC retention time (minutes): 3.919.

Preparation of Additional Compounds

Utilizing the appropriate substituted aniline reagent as described in part B of this example, and the appropriate azabicyclo[3.1.0]hexane as described in part C of this example, the following compounds were prepared:

Compound 2: {3-[4-(3-Methyl-4-phenoxy-phenylamino)-pyrido[3,4-d]pyrimidin-6-yl]-3-aza-bicyclo[3.1.0]hex-6-yl}-methanol; (M.S. (m+1): 440); HPLC retention time (minutes): 6.084.

Compound 3: [6-(6-Dimethylamino-3-aza-bicyclo[3.1.0]hex-3-yl)-pyrido[3,4-d]pyrimidin-4-yl]-(3-methyl-4-phenoxy-phenyl)-amine (M.S. (m+1): 453); HPLC retention time (minutes): 6.283.

Compound 4: {3-[4-(3-Methoxy-4-phenoxy-phenylamino)-pyrido[3,4-d]pyrimidin-6-yl]-3-aza-bicyclo[3.1.0]hex-6-yl}-methanol (M.S. (m+1): 456); HPLC retention time (minutes): 5.646.

Compound 5: [6-(6-Amino-3-aza-bicyclo[3.1.0]hex-3-yl)-pyrido[3,4-d]pyrimidin-4-yl]-(3-methyl-4-phenoxy-phenyl)-amine (M.S. (m+1): 425); HPLC retention time (minutes): 5.018.

Compound 6: [6-(6-Amino-3-aza-bicyclo[3.1.0]hex-3-yl)-pyrido[3,4-d]pyrimidin-4-yl]-[3-chloro-4-(pyridin-3-yloxy)-phenyl]-amine (M.S. (m+1): 446); HPLC retention time (minutes): 4.099.

Compound 7: [6-(6-Amino-3-aza-bicyclo[3.1.0]hex-3-yl)-pyrido[3,4-d]pyrimidin-4-yl]-[3-methyl-4-(6-methyl-pyridin-3-yloxy)-phenyl]-amine (M.S. (m+1): 440) HPLC retention time (minutes): 3.917.

EXAMPLE 2

Compound 8: N-(3-{4-[3-Methyl-4-(pyridin-3-yloxy)-phenylamino]-pyrido[3,4-d]pyrimidin-6-yl}-3-aza-bicyclo[3.1.0]hex-6-yl)-2-methylsulfanyl-acetamide. To a solution of 34 µL (0.39 mmol) of methylthioacetic acid in 1 mL of methylene chloride in a ice/brine bath was added 62.8 mg (0.39 mmol) of carbonyl diimidazole. The mixture was stirred for 15 minutes and 150 mg (0.353 mmol) of [6-(6-amino-3-aza-bicyclo[3.1.0]hex-3-yl)-pyrido[3,4-d]pyrimidin-4-yl]-[3-methyl-4-(pyridin-3-yloxy)-phenyl]-amine was added along with additional methylene chloride to aid stirring. After stirring for 1 hour, the reaction was filtered and the precipitate was washed with methylene chloride and air dried. The solid was recrystallized from methanol/methylene chloride to afford 112 mg (62%) of the title compound. $^1$H NMR (CDCl$_3$): δ 8.83 (s, 1), 8.35 (s, 1), 8.25 (m, 2), 7.72 (m, 1), 7.62 (m, 1), 7.24 (m, 2), 7.07 (s, 1), 6.91 (d, 1), 3.92 (d, 2), 3.52 (m, 2), 3.13 (s, 2), 2.48 (m, 1), 2.22 (s, 3), 2.10 (s, 3), 1.89 (m, 2), M.S. (m+1): 514. HPLC retention time (minutes): 5.154.

Following Example 2, and using the appropriate carboxylic acid, the following compounds were prepared:

Compound 9: Thiophene-2-carboxylic acid (3-{4-[3-methyl-4-(pyridin-3-yloxy)-phenylamino]-pyrido[3,4-d]pyrimidin-6-yl}-3-aza-bicyclo[3.1.0]hex-6-yl)-amide (M.S. (m+1): 536); HPLC retention time (minutes): 5.831; and Compound 10: N-(3-{4-[3-Chloro-4-(pyridin-3-yloxy)-phenylamino]-pyrido[3,4-d]pyrimidin-6-yl}-3-aza-bicyclo[3.1.0]hex-6-yl)-acetamide (M.S. (m+1): 488) HPLC retention time (minutes): 4.978.

Following Example 2, and using [6-(6-Amino-3-aza-bicyclo[3.1.0]hex-3-yl)-pyrido[3,4-d]pyrimidin-4-yl]-[3-methyl-4-(6-methyl-pyridin-3-yloxy)-phenyl]-amine and the appropriate carboxylic acid, the following compounds were prepared:

Compound 11: Thiophene-2-carboxylic acid (3-{4-[3-methyl-4-(6-methyl-pyridin-3-yloxy)-phenylamino]-pyrido[3,4-d]pyrimidin-6-yl}-3-aza-bicyclo[3.1.0]hex-6-yl)-amide (M.S. (m+1): 550); HPLC retention time (minutes): 6.050;

Compound 12: N-(3-{4-[3-Methyl-4-(6-methyl-pyridin-3-yloxy)-phenylamino]-pyrido[3,4-d]pyrimidin-6-yl}-3-aza-bicyclo[3.1.0]hex-6-yl)-2-methylsulfanyl-acetamide (M.S. (m+1): 528); HPLC retention time (minutes): 5.393;

Compound 13: 2-Methoxy-N-(3-{4-[3-methyl-4-(6-methyl-pyridin-3-yloxy)-phenylamino]-pyrido[3,4-d]pyrimidin-6-yl}-3-aza-bicyclo[3.1.0]hex-6-yl)-acetamide (M.S. (m+1): 512); HPLC retention time (minutes): 5.077; and Compound 14: N-(3-{4-[3-Methyl-4-(6-methyl-pyridin-3-yloxy)-phenylamino]-pyrido[3,4-d]pyrimidin-6-yl}-3-aza-bicyclo[3.1.0]hex-6-yl)-acetamide (M.S. (m+1): 482) HPLC retention time (minutes): 4.871.

EXAMPLE 3

Compound 15: Cyclopropanecarboxylic acid {3-[4-(3-methyl-4-phenoxy-phenylamino)-pyrido[3,4-d]pyrimidin-6-yl]-3-aza-bicyclo[3.1.0]hex-6-yl}-amide. A solution of 107.4 mg (0.25 mmol) of [6-(6-amino-3-aza-bicyclo[3.1.0]hex-3-yl)-pyrido[3,4-d]pyrimidin-4-yl]-(3-methyl-4-phenoxy-phenyl)-amine and 35.2 $\mu$L (0.25 mmol) of triethylamine in 0.5 mL of methylene chloride in an ice/brine bath was treated with 24.1 $\mu$L of cyclopropanecarbonyl chloride. The reaction was allowed to warm to room temperature and stirred for 1 hour. The mixture was diluted with chloroform and washed with 2×50 mL of saturated sodium bicarbonate. The organics were dried over sodium sulfate, filtered and concentrated under vacuum. The residue was recrystallized from ethyl acetate to afford 91.7 mg (73%) of the title compound. $^1$H NMR (CDCl$_3$): δ 8.78 (s, 1), 8.37 (s, 1), 7.63 (m, 1), 7.53 (m, 1), 7.26 (m, 2), 6.95 (m, 1), 6.89 (m, 3), 6.79 (s, 1), 3.87 (d, 2), 3.48 (m, 2), 2.38 (m, 1), 2.21 (s, 3), 184 (m, 2), 1.33 (m, 1), 0.89 (m, 2), 0.72 (m, 2). M.S. (m+1): 493; HPLC retention time (minutes): 6.672.

Following Example 3, and using acetyl chloride instead of cyclopropanecarbonylchloride, the following compound was prepared:

Compound 16: N-{3-[4-(3-Methyl-4-phenoxy-phenylamino)-pyrido[3,4-d]pyrimidin-6-yl]-3-aza-bicyclo[3.1.0]hex-6-yl}-acetamide (M.S. (m+1): 467) HPLC retention time (minutes):6.069.

Following example 3, and using [6-(6-Amino-3-aza-bicyclo[3.1.0]hex-3-yl)-pyrido[3,4-d]pyrimidin-4-yl]-[3-methyl-4-(pyridin-3-yloxy)-phenyl]-amine) and the appropriate acid chloride or sulfonyl chloride, the following compounds were prepared:

Compound 17: N-(3-{4-[3-Methyl-4-(pyridin-3-yloxy)-phenylamino]-pyrido[3,4-d]pyrimidin-6-yl}-3-aza-bicyclo[3.1.0]hex-6-yl)-acetamide (M.S. (m+1): 468); HPLC retention time (minutes):4.676;

Compound 18: 2-Methoxy-N-(3-{4-[3-methyl-4-(pyridin-3-yloxy)-phenylamino]-pyrido[3,4-d]pyrimidin-6-yl}-3-aza-bicyclo[3.1.0]hex-6-yl)-acetamide (M.S. (m+1): 498); HPLC retention time (minutes):4.836;

Compound 19: Cyclopropanecarboxylic acid (3-{4-[3-methyl-4-(pyridin-3-yloxy)-phenylamino]-pyrido[3,4-d]pyrimidin-6-yl}-3-aza-bicyclo[3.1.0]hex-6-yl)-amide (M.S. (m+1): 494); HPLC retention time (minutes): 5.170; and Compound 20: N-(3-{4-[3-Methyl-4-(pyridin-3-yloxy)-phenylamino]-pyrido[3,4-d]pyrimidin-6-yl}-3-aza-bicyclo[3.1.0]hex-6-yl)-methanesulfonamide (M.S. (m+1): 504) HPLC retention time (minutes):5.150.

Following example 3, and using [6-(6-Amino-3-aza-bicyclo[3.1.0]hex-3-yl)-pyrido[3,4-d]pyrimidin-4-yl]-[3-methyl-4-(6-methyl-pyridin-3-yloxy)-phenyl]-amine and methanesulfonyl chloride, the following compound was prepared:

Compound 21: N-(3-{4-[3-Methyl-4-(6-methyl-pyridin-3-yloxy)-phenylamino]-pyrido[3,4-d]pyrimidin-6-yl}-3-aza-bicyclo[3.1.0]hex-6-yl)-methanesulfonamide (M.S. (m+1): 518) HPLC retention time (minutes):5.329.

Compounds 1–21 described above have been tested according to the methods described herein and found to be potent inhibitors of the erbB2 receptor kinase, with characteristic IC$_{50}$ values in the range from about 1 nM to about 1 $\mu$M.

Additional compounds which are potent inhibitors of the erb2 receptor kinase may also be prepared according to Example 1, utilizing the appropriate substituted aniline reagent in part B of Example 1 and the appropriate (optionally substituted) azetidine or azabicyclic compound in part C of Example 1, for example:

Compound 22: [6-(3-Methoxy-azetidin-1-yl)-pyrido[3,4-d]pyrimidin-4-yl]-[3-methyl-4-(6-methyl-pyridin-3-yloxy)-phenyl]-amine (M.S. (m+1): 429.2; HPLC retention time (minutes): 6.07.

Compound 23: (1-{4-[3-Methyl-4-(6-methyl-pyridin-3-yloxy)-phenylamino]-pyrido[3,4-d]pyrimidin-6-yl}-azetidin-3-yl)-carbamic acid tert-butyl ester (M.S. (m+1): 514.2; HPLC retention time (minutes): 6.57.

Compound 24: 2-Methoxy-N-(1-{4-[3-methyl-4-(6-methyl-pyridin-3-yloxy)-phenylamino]-pyrido[3,4-d]pyrimidin-6-yl}-azetidin-3-yl)-acetamide (M.S. (m+1): 486.2; HPLC retention time (minutes):5.16.

Compound 25: [6-(3-Methanesulfonyl-azetidin-1-yl)-pyrido[3,4-d]pyrimidin-4-yl]-[3-methyl-4-(6-methyl-pyridin-3-yloxy)-phenyl]-amine (M.S. (m+1): 477.3; HPLC retention time (minutes):5.15.

Compound 26: [6-(6-Amino-3-aza-bicyclo[3.1.0]hex-3-yl)-pyrido[3,4-d]pyrimidin-4-yl]-[4-(2-fluoro-phenoxy)-3-methyl-phenyl]-amine (M.S. (m+1): 443.27; HPLC retention time (minutes):5.01.

Compound 27: [4-(2-Fluoro-phenoxy)-3-methyl-phenyl]-[6-(hexahydro-pyrrolo[3,4-c]pyrrol-2-yl)-pyrido[3,4-d]pyrimidin-4-yl]-amine (M.S. (m+1): 457.1; HPLC retention time (minutes):5.05.

Compound 28: [6-(6-Amino-3-aza-bicyclo[3.1.0]hex-3-yl)-pyrido[3,4-d]pyrimidin-4-yl]-(3-chloro-4-phenoxy-phenyl)-amine (M.S. (m+1): 445.23; HPLC retention time (minutes):5.17.

Compound 29: [6-(6-Amino-3-aza-bicyclo[3.1.0]hex-3-yl)-pyrido[3,4-d]pyrimidin-4-yl]-[4-(3-fluoro-phenoxy)-3-methoxy-phenyl]-amine (M.S. (m+1): 459.1; HPLC retention time (minutes):4.95.

Compound 30: [6-(6-Amino-3-aza-bicyclo[3.1.0]hex-3-yl)-pyrido[3,4-d]pyrimidin-4-yl]-[4-(2,6-difluorophenoxy)-3-methyl-phenyl]-amine (M.S. (m+1): 461.2; HPLC retention time (minutes):5.06.

What is claimed is:

1. A compound of formula 1

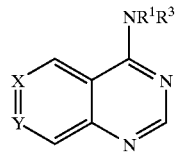

or a pharmaceutically acceptable salt, prodrug or hydrate thereof, wherein:
each $R^1$ and $R^2$ is independently H or $(C_1-C_6)$alkyl; wherein $R^3$ is $-(CR^1R^2)_m-R^4$, wherein m is an integer from 0 to 6;
wherein either X is N and Y is $CR^9$, or X is $CR^9$ and Y is N;
$R^4$ is aryl or heteroaryl, wherein the aryl or heteroaryl is optionally substituted on one carbon atom with $R^5$, $-Z^1R^5$, $-Z^1(CR^1R^2)_rR^5$ or $-(CR^1R^2)_nR^5$, wherein n is an integer from 0 to 4, optionally substituted on another carbon atom with $R^6$ and optionally substituted on any remaining carbon atoms independently with $R^8$;
$Z^1$ is $S(O)_j$ wherein j is an integer from 0 to 2, O, or $NR^1$, provided that when $-Z^1R^5$ is $-NR^1R^5$, $R^5$ is linked to N by a carbon atom;
each r independently is an integer from 1 to 4;
$R^5$ is aryl, heteroaryl or heterocyclyl, wherein the aryl, heteroaryl or heterocyclyl is optionally substituted on one carbon atom with $R^6$ and optionally substituted on up to three other carbon atoms independently with $R^8$, and wherein when $R^5$ is heterocyclyl, the heterocyclyl is optionally substituted on up to two nitrogen atoms independently with $R^7$;
each $R^6$ is independently $(C_1-C_6)$alkyl, $(C_2-C_6)$alkenyl, $(C_2-C_6)$alkynyl, $(C_3-C_8)$cycloalkyl, $(C_1-C_6)$alkoxy, $(C_1-C_6)$alkylthio, hydroxy$(C_1-C_6)$alkyl, trifluoromethyl, trifluoromethyl$(C_2-C_6)$alkyl, trifluoromethoxy, trifluoro$(C_2-C_6)$alkoxy, $-(CR^1R^2)_nO(C_1-C_6$ alkyl$)$, $-(CR^1R^2)_nS(O)_j(C_1-C_6$ alkyl$)$, halo, hydroxy, cyano, nitro, azido, amino, $-(CR^1R^2)_nNR^1R^7$, $-C(O)NR^1R^7$, $-NR^7C(O)R^{11}$, $-NR^7OR^{14}$, $-NR^7C(O)OR^{12}$, $-NR^7S(O)_jR^{14}$, $-C(O)R^{11}$, $-C(S)R^{11}$, $-C(O)OR^{12}$, $-OC(O)R^{11}$, $-SO_2NR^1R^7$, $-S(O)_jR^{11}$, $-CH=NOR^{14}$, $-(CR^1R^2)_jS(O)_jR^{11}$, $-Z^2-(CR^1R^2)_n(C_6-C_{10}$ aryl$)$, $-Z^2-(CR^1R^2)_n(C_6-C_{10}$ heteroaryl$)$, or $-Z^2-(CR^1R^2)_n(4-$ to 10-membered heterocyclic); wherein $Z^2$ is O, or $-(CR^1R^2)_n-$; wherein the alkyl, alkenyl, alkynyl, aryl, heteroaryl and heterocyclic moieties of the foregoing $R^6$ groups are optionally substituted with 1 to 3 substituents independently selected from halo, cyano, nitro, trifluoromethyl, trifluoromethoxy, azido, $-OR^{12}$, $-C(O)R^{12}$, $-C(O)OR^{12}$, $-OC(O)R^{12}$, $-NR^{13}C(O)R^{12}$, $-C(O)NR^1R^{13}$, $-(CR^1R^2)_nNR^1R^{13}$, and $-NR^{13}OR^{12}$, $C_1-C_6$ alkyl, $C_2-C_6$ alkenyl, $C_2-C_6$ alkynyl, $-(CR^1R^2)_t(C_6-C_{10}$ aryl$)$, and $-(CR^1R^2)_t(4$ to 10 membered heterocyclic); wherein each t is independently an integer from 0 to 5;
each $R^7$ is independently H, $(C_1-C_6)$alkyl, $(C_3-C_8)$ cycloalkyl, $-C(O)R^{11}$, $-C(S)R^{11}$, $-(CR^1R^2)_nO(C_1-C_6$ alkyl$)$, $-(CR^1R^2)_nS(O)_j(C_1-C_6$ alkyl$)$, $-(CR^1R^2)_rC(O)R^{11}$, $-(CR^1R^2)_nR^{11}$ or $-SO_2R^{11}$; wherein each v is independently an integer from 2 to 5;

each $R^8$ is independently $(C_1-C_6)$alkyl, $(C_2-C_6)$alkenyl, $(C_2-C_6)$alkynyl, $(C_3-C_8)$cycloalkyl, $(C_1-C_6)$alkoxy, $(C_1-C_6)$alkylthio, hydroxy$(C_1-C_6)$alkyl, trifluoromethyl, trifluoromethyl$(C_2-C_6)$alkyl, trifluoromethoxy, trifluoro$(C_2-C_6)$alkoxy, $-(CR^1R^2)_nO(C_1-C_6$ alkyl$)$, $-(CR^1R^2)_nS(O)_j(C_1-C_6$ alkyl$)$, halo, cyano, nitro, azido, amino, $-(CR^1R^2)_nNR^1R^7$, $-C(O)NR^1R^7$, $-NR^1C(O)R^{11}$, $-NR^1OR^2$, $-NR^1C(O)OR^{12}$, $-NR^1S(O)_jR^{14}$, $-C(O)R^{11}$, $-C(S)R^{11}$, $-C(O)OR^{12}$, $-OC(O)R^{11}$, $-SO_2NR^1R^7$, $-CH=NOR^{14}$, $-S(O)_jR^1$, or $-(CR^1R^2)_jS(O)_jR^1$, wherein the alkyl, alkenyl and alkynyl moieties of the foregoing $R^8$ groups are optionally substituted with 1 to 3 substituents independently selected from halo, cyano, nitro, trifluoromethyl, trifluoromethoxy, azido, $-OR^{12}$, $-C(O)R^{12}$, $-C(O)OR^{12}$, $-OC(O)R^{12}$, $-NR^7C(O)R^{12}$, $-C(O)NR^1R^{13}$, $-NR^1R^{13}$, and $-NR^{13}OR^{12}$, $C_1-C_6$ alkyl, $C_2-C_6$ alkenyl, $C_2-C_6$ alkynyl, $-(CR^1R^2)_t(C_6-C_{10}$ aryl$)$, and $-(CR^1R^2)_t(4$ to 10 membered heterocyclic);

$R^9$ is a fused-ring bicyclic, bridged bicyclic or spirobicylic group, wherein each ring in the bicyclic group is saturated or unsaturated or aromatic, wherein each ring in the bicyclic group optionally contains up to three heteroatoms selected from N, O, and S, and wherein each ring in the bicyclic group is optionally substituted on up to four atoms, wherein any optional carbon substituent is independently $R^{10}$, wherein any sp$^3$-hybridized nitrogen is optionally substituted with $R^7$; and provided that in $R^9$ the ring distal to the pyridopyrimidine of formula 1 does not comprise methylenedioxy or ethylenedioxy; or $R^9$ is azetidinyl substituted on one carbon with $R^{10}$;

each $R^{10}$ is independently $(C_1-C_6)$alkyl, $(C_2-C_6)$alkenyl, $(C_2-C_6)$alkynyl, $(C_3-C_8)$cycloalkyl, $(C_1-C_6)$alkoxy, $(C_1-C_6)$alkylthio, -hydroxy$(C_1-C_6)$alkyl, trifluoromethyl, trifluoromethyl$(C_2-C_6)$alkyl, trifluoromethoxy, trifluoro$(C_2-C_6)$alkoxy, $-(CR^1R^2)_nO(C_1-C_6$ alkyl$)$, $-(CR^1R^2)_nS(O)_j(C_1-C_6$ alkyl$)$, halo, hydroxy, cyano, nitro, azido, amino, $-(CR^1R^2)_nNR^1R^7$, $-C(O)NR^1R^7$, $-NR^7C(O)R^{11}$, $-NR^7OR^{14}$, $-NR^7C(O)OR^{12}$, $-NR^7S(O)_jR^{14}$, $-C(O)R^{11}$, $-C(S)R^{11}$, $-C(O)OR^{12}$, $-OC(O)R^{11}$, $-SO_2NR^1R^7$, $-S(O)_jR^{11}$, $-CH=NOR^{14}$, $-(CR^1R^2)_nS(O)_jR^{11}$, $-Z^2-(CR^1R^2)_n(C_6-C_{10}$ aryl$)$, $-Z^2-(CR^1R^2)_n(C_6-C_{10}$ heteroaryl$)$, or $-Z^2-(CR^1R^2)_n(4-$ to 10-membered heterocyclic), wherein $Z^2$ is O, or $-(CR^1R^2)_n-$; wherein the alkyl, alkenyl, alkynyl, aryl, heteroaryl and heterocyclic moieties of the foregoing $R^{10}$ groups are optionally substituted with 1 to 3 substituents independently selected from halo, cyano, nitro, trifluoromethyl, trifluoromethoxy, azido, $-OR^{12}$, $-C(O)R^{12}$, $-C(O)OR^{12}$, $-OC(O)R^{12}$, $-NR^{13}C(O)R^{12}$, $-C(O)NR^1R^{13}$, $-(CR^1R^2)_nNR^1R^{13}$, and $-NR^7OR^{14}$, $C_1-C_6$ alkyl, $C_2-C_6$ alkenyl, $C_2-C_6$ alkynyl, $-(CR^1R^2)_t(C_6 C_{10}$ aryl$)$, and $-(CR^1R^2)_t(4$ to 10 membered heterocyclic), wherein t is an integer from 0 to 5;

each $R^{11}$ is independently H, $(C_1-C_6)$alkyl, $(C_3-C_8)$ cycloalkyl, -hydroxy$(C_2-C_6)$alkyl, trifluoromethyl, trifluoro$(C_2-C_6)$alkyl, $-(CR^1R^2)_nO(C_1-C_6$ alkyl$)$, $-(CR^1R^2)_nS(O)_j(C_1-C_6$ alkyl$)$, $-(CR^1R^2)_nNR^1R^{13}$, $-(CR^1R^2)_rC(O)NR^1R^{13}$, $-(CR^1R^2)_rC(O)R^{12}$, $-(CR^1R^2)_rC(S)R^{12}$, $-(CR^1R^2)_rC(O)OR^{12}$, $-(CR^1R^2)_nS(O)_jR^{12}$, $-(CR^1R^2)_n-(C_6-C_{10}$aryl$)$, $-(CR^1R^2)_n-C_6-C_{10}$heteroaryl$)$, $-(CR^1R^2)_n-(4$ to 10 membered heterocyclic), wherein the alkyl, aryl, heteroaryl and heterocyclic moieties of the foregoing $R^{11}$ groups are optionally substituted with 1 to 3 substituents independently selected from halo, cyano, nitro, trifluoromethyl, trifluoromethoxy, azido, —$OR^2$, —$C(O)R^{12}$, —$C(O)OR^{12}$, —$OC(O)R^{12}$, —$NR^{13}C(O)R^{12}$, —$C(O)NR^1R^{13}$, —$NR^1R^{13}$, —$NR^{13}OR^{14}$, $C_1$–$C_6$ alkyl, $C_2$–$C_6$ alkenyl, $C_2$–$C_6$ alkynyl, —$(CR^1R^2)_t(C_6$–$C_{10}$ aryl), and —$(CR^1R^2)_t$(4 to 10 membered heterocyclic), wherein t is an integer from 0 to 5;

each $R^{12}$ is independently H, $(C_1$–$C_6)$alkyl, $(C_3$–$C_8)$ cycloalkyl, -hydroxy$(C_2$–$C_6)$alkyl, trifluoromethyl, trifluoro$(C_2$–$C_6)$alkyl, —$(CR^1R^2)_n(C_1$–$C_6$ alkyl), —$(CR^1R^2)_nO(C_1$–$C_6$ alkyl), —$(CR^1R^2)_nS(O)_j(C_1$–$C_6$ alkyl), —$(CR^1R^2)_rNR^1R^{14}$, —$(CR^1R^2)_n$—$(C_6$–$C_{10}$aryl), —$(CR^1R^2)_n$—$(C_6$–$C_{10}$heteroaryl), —$(CR^1R^2)_n$—(4 to 10 membered heterocyclic), wherein the alkyl, aryl, heteroaryl and heterocyclic moieties of the foregoing $R^{12}$ groups are optionally substituted with 1 to 3 substituents independently selected from halo, cyano, nitro, trifluoromethyl, trifluoromethoxy, azido, —$OR^{14}$, —$C(O)R^{14}$, —$C(O)OR^1$, —$OC(O)R^{14}$, —$NR^2C(O)R^{14}$, —$C(O)NR^1R^{14}$, —$NR^1R^{14}$, —$NR^2OR^1$, $C_1$–$C_6$ alkyl, $C_2$–$C_6$ alkenyl, $C_2$–$C_6$ alkynyl, —$(CR^1R^2)_t(C_6$–$C_{10}$ aryl), and —$(CR^1R^2)_t$(4 to 10 membered heterocyclic), wherein t is an integer from 0 to 5;

each $R^{13}$ is independently H, $(C_1$–$C_6)$alkyl, $(C_3$–$C_8)$ cycloalkyl, —$C(O)R^{14}$, —$C(S)R^{14}$, —$(CR^1R^2)_vO(C_1$–$C_6$ alkyl), —$(CR^1R^2)_vS(C_1$–$C_6$ alkyl), —$(CR^1R^2)_rC(O)R^{14}$, —$(CR^1R^2)_mR^{14}$ or —$SO_2R^{14}$; wherein v is an integer from 2 to 5;

each $R^{14}$ is independently H, $(C_1$–$C_6)$alkyl, $(C_3$–$C_8)$ cycloalkyl, trifluoromethyl, trifluoromethyl$(C_2$–$C_6)$ alkyl, —$(CR^1R^2)_n(C_6$–$C_{10}$ aryl), —$(CR^1R^2)_n(C_6$–$C_{10}$ heteroaryl), or —$(CR^1R^2)_n$(4- to 10-membered heterocyclic), wherein the alkyl, aryl, heteroaryl and heterocyclic moieties of the foregoing $R^{14}$ groups are optionally substituted with 1 to 3 substituents independently selected from $C_1$–$C_6$ alkyl, $C_1$–$C_6$ alkoxy, amino, hydroxy, halo, cyano, nitro, trifluoromethyl, trifluoromethoxy;

and wherein any of the above substituents $R^1$ through $R^{14}$ comprising a $CH_3$ (methyl), $CH_2$ (methylene), or CH (methine) group which is not substituted with halogen, SO or $SO_2$, or attached to a N, O or S atom, optionally bears on said methyl, methylene or methine group a substituent selected from hydroxy, halo, —$(C_1$–$C_6)$ alkyl, —$O((C_1$–$C_6)$alkyl), —SH, —$S((C_1$–$C_6)$alkyl) —$SR^1$, —$NH_2$, —$NH((C_1$–$C_6)$alkyl), and —$N((C_1$–$C_6)$alkyl)$_2$;

provided that in $R^4$, $R^5$ and any ring in $R^9$, two O atoms, two $S(O)_j$ moieties, an O atom and a $S(O)_j$ moiety, an N atom and an S atom, or an N atom and an O atom are not attached directly to each other within said ring.

2. The compound of claim 1, wherein $R^9$ is a bridged bicyclic ring optionally substituted with from one to three $R^{10}$.

3. The compound of claim 2, wherein $R^9$ is an azabicyclic group containing 5–9 atoms attached to the pyridopyrimidine ring of formula 1 through a nitrogen atom, optionally substituted with from one to three $R^{10}$.

4. The compound of claim 3, wherein $R^9$ is azabicycloalkyl containing from 5 to 9 atoms, optionally substituted with from one to three $R^{10}$.

5. The compound of claim 4, wherein $R^9$ is azabicyclo[3.1.0]hexyl optionally substituted with from one to three $R^{10}$.

6. The compound of claim 1, wherein $R^9$ is azetidinyl optionally substituted on one carbon with one $R^{10}$, wherein the azetidinyl is attached to the pyridopyrimidine ring of formula 1 through a nitrogen atom.

7. The compound of claim 1, wherein m is 0 and $R^4$ is phenyl optionally substituted on one atom with -$Z^1R^5$, optionally substituted on one other atom with $R^6$, and optionally substituted on up to three other atoms independently with $R^8$.

8. The compound of claim 7, wherein $R^9$ is azetidinyl optionally substituted on one carbon with $R^{10}$, or $R^9$ is azabicyclo[3.1.0]hexyl optionally substituted with from one to three $R^{10}$, wherein the azetidinyl or the azabicyclo[3.1.0.] hexyl group is attached to the pyridopyrimidine ring of formula 1 through a nitrogen atom.

9. The compound of claim 7, wherein $R^4$ is phenyl substituted on one atom with -$Z^1R^5$ and optionally substituted on one other atom with $R^6$.

10. The compound of claim 9, wherein $Z^1$ is oxygen.

11. The compound of claim 10, wherein $R^9$ is an azabicyclic group containing 5–9 atoms attached to the pyridopyrimidine ring of formula 1 through a nitrogen atom, optionally substituted with from one to three $R^{10}$.

12. The compound of claim 11, wherein $R^5$ is phenyl, pyridin-2-yl or pyridin-3-yl, wherein the phenyl, pyridin-2-yl or pyridin-3-yl is optionally substituted on up to three atoms independently with $R^8$.

13. The compound of claim 12, wherein $R^9$ is azabicycloalkyl containing from 5 to 9 atoms, optionally substituted with from one to three $R^{10}$.

14. The compound of claim 12, wherein each $R^6$ is independently $(C_1$–$C_3)$alkyl, $(C_1$–$C_3)$alkenyl, $(C_1$–$C_3)$ alkynyl, $(C_1$–$C_3)$alkoxy, $(C_1$–$C_3)$alkylthio, trifluoromethyl, trifluoromethoxy halo, cyano, nitro, azido or amino.

15. The compound of claim 12, wherein each $R^8$ is independently $(C_1$–$C_3)$alkyl, $(C_1$–$C_3)$alkenyl, $(C_{C3})$alkynyl, $(C_1$–$C_3)$alkoxy, $(C_1$–$C_3)$alkylthio, trifluoromethyl, trifluoromethoxy or halo.

16. The compound of claim 12, wherein $R^9$ is azabicyclo[3.1.0]hexyl substituted with one $R^{10}$, wherein $R^{10}$ is $(C_1$–$C_6)$alkyl, $(C_1$–$C_6)$alkoxy, $(C_1$–$C_6)$alkylthio, trifluoromethyl, trifluoromethoxy, -hydroxy$(C_1$–$C_6)$alkyl, —$(CR^1R^2)_nO(C_1$–$C_6$ alkyl), halo, amino, —$NR^7C(O)R^{11}$, —$NR^7S(O)_2R^{14}$, —$SO_2NR^1R^7$, —$S(O)_jR^{11}$, or —$(CR^1R^2)_nS(O)_jR^{11}$.

17. The compound of claim 12, wherein $R^5$ is phenyl optionally substituted on up to three atoms independently with $R^8$.

18. The compound of claim 17 selected from:

{3-[4-(3-Methyl-4-phenoxy-phenylamino)-pyrido[3,4-d]pyrimidin-6-yl]-3-aza-bicyclo[3.1.0]hex-6-yl}-methanol;

[6-(6-Dimethylamino-3-aza-bicyclo[3.1.0]hex-3-yl)-pyrido[3,4-d]pyrimidin-4-yl]-(3-methyl-4-phenoxy-phenyl)-amine;

{3-[4-(3-Methoxy-4-phenoxy-phenylamino)-pyrido[3,4-d]pyrimidin-6-yl]-3-aza-bicyclo[3.1.0]hex-6-yl}-methanol;

[6-(6-Amino-3-aza-bicyclo[3.1.0]hex-3-yl)-pyrido[3,4-d]pyrimidin-4-yl]-(3-phenoxy-phenyl)-amine.

19. The compound of claim 17, wherein $R^{10}$ is —$NR^7C(O)R^{11}$.

20. The compound of claim 19 selected from:

N-{3-[4-(3-Methyl-4-phenoxy-phenylamino)-pyrido[3,4-d]pyrimidin-6-yl]-3-aza-bicyclo[3.1.0]hex-6-yl}-acetamide; and Cyclopropanecarboxylic acid {3-[4-(3-methyl-4-phenoxy-phenylamino)-pyrido[3,4-d]pyrimidin-6-yl]-3-aza-bicyclo[3.1.0]hex-6-yl}-amide.

21. The compound of claim 12, wherein $R^5$ is pyridin-3-yl optionally substituted on up to three atoms independently with $R^8$.

22. The compound of claim 21 selected from:

[6-(6-Amino-3-aza-bicyclo[3.1.0]hex-3-yl)-pyrido[3,4-d]pyrimidin-4-yl]-[3-methyl-4-(pyridin-3-yloxy)-phenyl]-amine;

[6-(6-Amino-3-aza-bicyclo[3.1.0]hex-3-yl)-pyrido[3,4-d]pyrimidin-4-yl]-[3-chloro-4-(pyridin-3-yloxy)-phenyl]-amine;

[6-(6-Amino-3-aza-bicyclo[3.1.0]hex-3-yl)-pyrido[3,4-d]pyrimidin-4-yl]-[3-methyl-4-(6-methyl-pyridin-3-yloxy)-phenyl]-amine;

N-(3-{4-[3-Methyl-4-(pyridin-3-yloxy)-phenylamino]-pyrido[3,4-d]pyrimidin-6-yl}-3-aza-bicyclo[3.1.0]hex-6-yl)-methanesulfonamide; and N-(3-{4-[3-Methyl-4-(6-methyl-pyridin-3-yloxy)-phenylamino]-pyrido[3,4-d]pyrimidin-6-yl}-3-aza-bicyclo[3.1.0]hex-6-yl)-methanesulfonamide.

23. The compound of claim 21, wherein $R^{10}$ is —$NR^7C(O)R^{11}$.

24. The compound of claim 23 selected from:

N-(3-{4-[3-methyl-4-(pyridin-3-yloxy)-phenylamino]-pyrido[3,4-d]pyrimidin-6-yl}-3-aza-bicyclo[3.1.0]hex-6-yl)-acetamide;

2-Methoxy-N-(3-{4-[3-methyl-4-(pyridin-3-yloxy)-phenylamino]-pyrido[3,4-d]pyrimidin-6-yl}-3-aza-bicyclo[3.1.0]hex-6-yl)-acetamide;

Cyclopropanecarboxylic acid (3-{4-[3-methyl-4-(pyridin-3-yloxy)-phenylamino]-pyrido[3,4-d]pyrimidin-6-yl}-3-aza-bicyclo[3.1.0]hex-6-yl)-amide;

Thiophene-2-carboxylic acid (3-{4-[3-methyl-4-(pyridin-3-yloxy)-phenylamino]-pyrido[3,4-d]pyrimidin-6-yl}-3-aza-bicyclo[3.1.0]hex-6-yl)-amide;

N-(3-{4-[3-Methyl-4-(pyridin-3-yloxy)-phenylamino]-pyrido[3,4-d]pyrimidin-6-yl}-3-aza-bicyclo[3.1.0]hex-6-yl)-2-methylsulfanyl-acetamide;

N-(3-{4-[3-Chloro-4-(pyridin-3-yloxy)-phenylamino]-pyrido[3,4-d]pyrimidin-6 -yl}-3-aza-bicyclo[3.1.0]hex-6-yl)-acetamide;

Thiophene-2-carboxylic acid (3-{4-[3-methyl-4-(6-methyl-pyridin-3 -yl oxy)-phenylamino]-pyrido[3,4-d]pyrimidin-6-yl}-3-aza-bicyclo[3.1.0]hex-6-yl)-amide;

N-(3-{4-[3-Methyl-4-(6-methyl-pyridin-3-yloxy)-phenylamino]-pyrido[3,4-d]pyrimidin-6-yl}-3-aza-bicyclo[3.1.0]hex-6-yl)-2-methylsulfanyl-acetamide;

2-Methoxy-N-(3-{4-[3-methyl-4-(6-methyl-pyridin-3-yloxy)-phenylamino]-pyrido[3,4-d]pyrimidin-6-yl}-3-aza-bicyclo[3.1.0]hex-6-yl)-acetamide; and N-(3-{4-[3-Methyl-4-(6-methyl-pyridin-3-yloxy)-phenylamino]-pyrido[3,4-d]pyrimidin-6-yl}-3-aza-bicyclo[3.1.0]hex-6-yl)-acetamide.

25. The compound of claim 1 selected from:

[6-(3-Methoxy-azetidin-1-yl)-pyrido[3,4-d]pyrimidin-4-yl]-[3-methyl-4-(6-methyl-3-yloxy)-phenyl]-amine;

(1-{4-[3-Methyl-4-(6-methyl-pyridin-3-yloxy)-phenylamino]-pyrido[3,4-d]pyrimidin-6-yl}-azetidin-3-yl)-carbamic acid tert-butyl ester;

2-Methoxy-N-(1-{4-[3-methyl-4-(6-methyl-pyridin-3-yloxy)-phenylamino]-pyrido[3,4-d]pyrimidin-6-yl}-azetidin-3-yl)-acetamide;

[6-(3-Methanesulfonyl-azetidin-1-yl)-pyrido[3,4-d]pyrimidin-4-yl]-[3-methyl-4-(6-methyl-pyridin-3-yloxy)-phenyl]-amine;

[6-(6-Amino-3-aza-bicyclo[3.1.0]hex-3-yl)-pyrido[3,4-d]pyrimidin-4-yl]-[4-(2-fluorophenoxy)-3-methyl-phenyl]-amine;

[4-(2-Fluoro-phenoxy)-3-methyl-phenyl]-[6-(hexahydro-pyrrolo[3,4-c]pyrrol-2-yl)-pyrido[3,4-d]pyrimidin-4-yl]-amine;

[6-(6-Amino-3-aza-bicyclo[3.1.0]hex-3-yl)-pyrido[3,4-d]pyrimidin-4-yl]-(3-chloro-4-phenoxy-phenyl)-amine;

[6-(6-Amino-3-aza-bicyclo[3.1.0]hex-3-yl)-pyrido[3,4-d]pyrimidin-4-yl]-[4-(3-fluorophenoxy)-3-methoxy-phenyl]-amine; and

[6-(6-Amino-3-aza-bicyclo[3.1.0]hex-3-yl)-pyrido[3,4-d]pyrimidin-4-yl]-[4-(2,6-difluorophenoxy)-3-methyl-phenyl]-amine.

26. A method of treating pancreatitis in a mammal which comprises administering to said mammal a therapeutically effective amount of a compound of claim 1.

27. A method of preventing blastocyte implantation in a mammal which comprises administering to said mammal a therapeutically effective amount of a compound of claim 1.

28. A process for preparing a compound of claim 1, which comprises reacting a compound of formula 2

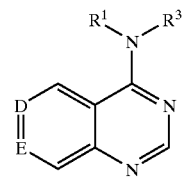

with $R^9$, wherein $R^9$ is an azetidinyl or azabicyclic group, in a polar solvent with heating, wherein either D is C—F or C—Cl and E is N, or D is N and E is C—F or C—Cl.

29. A pharmaceutical composition which comprises the compound of claim 1 and a pharmaceutically acceptable carrier.

* * * * *